(12) United States Patent
Kelly et al.

(10) Patent No.: US 7,718,182 B2
(45) Date of Patent: May 18, 2010

(54) **POLYPEPTIDES FOR INDUCING A PROTECTIVE IMMUNE RESPONSE AGAINST *STAPHYLOCOCCUS AUREUS***

(75) Inventors: Rosemarie Kelly, Westfield, NJ (US); Loren D. Schultz, Harleysville, PA (US); Mark A. Miller, Wyndmoor, PA (US); Mark D. Yeager, Saddle River, NJ (US); Tessie McNeely, Gwynedd Valley, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 11/795,538

(22) PCT Filed: Jan. 17, 2006

(86) PCT No.: PCT/US2006/001665

§ 371 (c)(1),
(2), (4) Date: Jul. 18, 2007

(87) PCT Pub. No.: WO2006/078680

PCT Pub. Date: Jul. 29, 2006

(65) Prior Publication Data

US 2008/0131447 A1 Jun. 5, 2008

Related U.S. Application Data

(60) Provisional application No. 60/645,811, filed on Jan. 21, 2005.

(51) Int. Cl.
| | |
|---|---|
| A61K 39/085 | (2006.01) |
| C12P 21/04 | (2006.01) |
| C07H 21/02 | (2006.01) |
| C07H 21/04 | (2006.01) |
| C07K 14/31 | (2006.01) |

(52) U.S. Cl. ............... 424/243.1; 424/185.1; 424/192.1; 536/23.1; 536/23.5; 536/23.7; 435/69.1; 435/69.5; 435/69.7; 530/350

(58) Field of Classification Search ........................ None
See application file for complete search history.

(56) References Cited

U.S. PATENT DOCUMENTS

| 6,380,370 B1 | 4/2002 | Doucette-Stamm et al. | |
| 6,872,563 B1 * | 3/2005 | Beckwith et al. | ......... 435/252.3 |

FOREIGN PATENT DOCUMENTS

| EP | 0 786 519 A1 | 7/1997 |
| WO | WO97/30070 | 8/1997 |
| WO | WO01/34809 A2 | 5/2001 |
| WO | WO01/70955 A2 | 9/2001 |
| WO | WO01/98499 A2 | 12/2001 |
| WO | WO02/34771 A2 | 5/2002 |
| WO | WO02/059148 A2 | 8/2002 |
| WO | WO02/077183 A2 | 10/2002 |
| WO | WO02/094868 A2 | 11/2002 |
| WO | 2004/013166 A2 | 2/2004 |

OTHER PUBLICATIONS

Houghten et al. (Vaccines, 1986, Edited by Fred Brown: Cold Spring Harbor Laboratory).*
(Lederman et al (Molecular Immunology 28:1171-1181, 1991).*
Li et al (Proc. Natl. Acad. Sci. USA 77:3211-3214, 1980).*
Armstrong et al., 'A homologue to the *Escherichia coli* alkyl hydroperoxide reductase AhpC is induced by osmotic upshock in *Staphylococcus aureus*', Microbiology, vol. 141, pp. 1655-1661 (1995).
Baba et al., 'Genome and virulence determinants of high virulence community-acquired MRSA', Lancet, vol. 359, pp. 1819-1827 (2002).
Chae et al., 'Cloning and sequencing of thiol-specific antioxidant from mammalian brain: Alkyl hydroperoxide reductase and thiol-speicific antioxidant define a large family of antioxidant enzymes', Proc. Natl. Acad. Sci. USA, vol. 91, pp. 7017-7021 (1994).
Enright et al., 'The evolutionary history of methicillin-resistant *Staphylococcus aureus* (MRSA)' PNAS, vol. 99, No. 11, pp. 7687-7692 (2002).
Etz et al., 'Identification of in vivo expressed vaccine candidate antigens from *Staphylococcus aureus*', PNAS, vol. 99, No. 10, pp. 6573-6578 (2002).
GenBank NCBI, Accession X85029, GI 706812.
GenBank NCBI, Accession U92441, GI 1916315.
Josefsson et al., 'Protection against Experimental *Staphylococcus aureus* Arthritis by Vaccination with Clumping Factor A, a Novel Virulence Determinant', The Journal of Infectious Diseased, vol. 184, pp. 1572-1580 (2001).
Kuroda et al., 'Whole genome sequencing of meticillin-resistant *Staphylococcus aureus*', Lancet, vol. 357, pp. 1225-1240 (2001).
Liang et al., 'Baculovirus expression cassette vectors for rapid production of complete human IgG from phage display selected antibody fragments', Immunol. Methods, vol. 247, pp. 119-130 (2001).

(Continued)

*Primary Examiner*—Robert B Mondesi
*Assistant Examiner*—Padma V Baskar
(74) *Attorney, Agent, or Firm*—Alysia A. Finnegan; Laura M. Ginkel; Sheldon O. Heber

(57) ABSTRACT

The present invention features polypeptides comprising an amino acid sequence structurally related to SEQ ID NO: 1 or a fragment thereof, *S. aureus* AhpC-AhpF compositions, and uses of such polypeptides and compositions. SEQ ID NO: 1 has a full length *S. aureus* AhpC sequence. A derivative of SEQ ID NO: 1 containing an amino His-tag and three additional carboxyl amino acids was found to produce a protective immune response against *S. aureus*.

MGHHHHHHHHHHSSGHIEGRHMSLINKEILPFTAQAFDPKKDQFKEVTQE
DLKGSWSVVCFYPADFSFVCPTELEDLQNQYEELQKLGVNVFSVSTDTHF
VHKAWHDHSDAISKITYTMIGDPSQTITRNDVLDEATGLAQRGTFIIDPD
GVVQASEINADGIGRDASTLAHKIKAAQYVRKNPGEVCPAKWEEGAKTLQ
PGLDLVGKIAEQ

13 Claims, 4 Drawing Sheets

OTHER PUBLICATIONS

Mamo et al., 'Vaccination with *Staphylococcus aureus* fibrinogen binding proteins (FgBPs) reduces colonisation of *S. aureus* in a mouse mastitis model', FEMS Immunology and Medical Microbiology, vol. 10, pp. 47-54 (1994).

Nilsson et al., 'Vaccination with a Recombinant Fragment of Collagen Adhesin Provides Protection against *Staphylococcus Aureus*—mediated Septic Death', J. Clin. Invest., vol. 101, pp. 2640-2649 (1998).

Ohta et al., 'Nucleotide Substitutions in *Staphylococcus aureus* Strains, Mu50, Mu3, and N315', DNA Research, vol. 11, pp. 51-56 (2004).

Shinefield, et al., 'Use of a *Staphylococcus aureus* Conjugate Vaccine in Patients Receiving Hemodialysis', New England Journal Medicine, vol. 346, No. 7, pp. 491-496 (2002).

Vogel, F.R., 'Improving Vaccine Performance with Adjuvants', Clinical Infectious Diseases 30 (suppl. 3) S266-270 (2000).

Yan et al., 'Immune Response to a 26-kDa Protein, Alkyl Hydroperoxide Reductase, in Helicobacter pylori-Infected Mongolian Gerbil Model', Helicobacter, vol. 6, pp. 274-282 (2001).

Accession No. F89804, Kuroda et al., PIR—The PIR (Protein Information Resource) database, May 10, 2001.

Hecker et al. "Proteomics of *Staphylococcus aureus*-current state and future challenges", Journal of Chromatography B, 2003, vol. 787, pp. 179-195.

Vytvytska et al. "Identification of vaccine candidate antigens of *Staphylococcus aureus* by serological proteome analysis", Proteomics, 2002, vol. 2, pp. 580-590.

* cited by examiner

MGHHHHHHHHHHSSGHIEGRH**MSLINKEILPFTAQAFDPKKDQFKEVTQEDLKGSWSVVCFYPADFSFVCPTELEDL
QNQYEELQKLGVNVFSVSTDTHFVHKAWHDHSDAISKITYTMIGDPSQTITRNFDVLDEATGLAQRGTFIIDPDGVV
QASEINADGIGRDASTLAHKIKAAQYVRKNPGEVCPAKWEEGAKTLQPGLDLVGKI**AEQ (SEQ ID NO: 2)

FIG. 1

SEQ ID NO: 1    MSLINKEILPFTAQAFDPKKDQFKEVTQEDLKGSWSVVCFYPADFSFVCPTELEDLQNQY
SEQ ID NO: 6    MSLINKEILPFTAQAYDPKKDEFKEVTQEDFKGSWNVVCFYPADFSFVCPTELEDLQNQY

SEQ ID NO: 1    EELQKLGVNVFSVSTDTHFVHKAWHDHSDAISKITYTMIGDPSQTITRNFDVLDEATGLA
SEQ ID NO: 6    AKLQELGVNVYSVSTDTHFVHKAWHDHSDAISKLEYSMIGDPSQTITRNFDVLDEETGLA

SEQ ID NO: 1    QRGTFIIDPDGVVQASEINADGIGRDASTLAHKIKAAQYVRKNPGEVCPAKWEEGAKTLQ
SEQ ID NO: 6    QRGTFIIDPDGVVQAAEINADGIGRDASTLVNKIKAAQYVRQHPGEVCPAKWEEGSESLQ

SEQ ID NO: 1    PGLDLVGKI
SEQ ID NO: 6    PGLDLVGKI

FIG. 2

ATGGGCCATCATCATCATCATCATCATCATCATCATCACAGCAGCGGCCATATCGAAGGTCGTCATATGTCATTAATTAA
CAAAGAAATCTTACCATTTACAGCGCAAGCTTTCGATCCAAAAAAGATCAATTTAAAGAAGTTACACAAGAAGATT
TAAAAGGTTCTTGGAGCGTAGTATGCTTCTATCCTGCTGACTTCTCATTCGTTTGTCCAACTGAATTAGAAGACTTA
CAAAACCAATATGAAGAATTACAAAAATTAGGCGTAAATGTATTCTCAGTATCAACTGATACTCACTTCGTACACAA
AGCATGGCATGACCATTCAGATGCAATTAGCAAAATCACTTACACTATGATTGGTGACCCATCACAAACAATCACTC
GTAATTTTGATGTATTAGATGAAGCTACTGGTTTAGCTCAACGTGGTACATTCATTATCGACCCAGACGGTGTTGTA
CAAGCATCTGAAATTAACGCTGACGGAATTGGCCGTGACGCTAGTACATTAGCTCACAAAATCAAAGCAGCTCAATA
TGTTCGTAAAAACCCTGGCGAAGTATGCCCAGCTAAATGGGAAGAAGGCGCTAAAACATTGCAACCTGGTTTAGATT
TAGTAGGTAAAATCGCTGAGCAATAA (SEQ ID NO: 5)

FIG. 3

```
ATGCTTAATGCTGATTTAAAACAACAACTTAAACAACTATTAGAACTAATGGAGGGCAACGTTGAATTCGTTGCCAG
CCTTGGTTCAGATGATAAATCCAAAGAACTTAAAGATTTGTTGACAGAAATTACTGATATGTCACCTAGACTATCTC
TTTCTGAAAAATCTTTAAAACGTACACCAAGTTTCTCAGTCAATCGTCCTGGCGAAGAAACAGGTGTAACATTTGCA
GGTATTCCATTAGGTCACGAGTTTAACTCACTTGTTTTAGCAATTTTACAGGTTAGTGGTCGTGCACCTAAAGAAAA
ACAGTCAATCATTGACCAAATTAAAAAATTAGAAGGTTCATTCCATTTTGAAACATTCATTAGTTTAACGTGTCAAA
AATGTCCTGATGTCGTTCAAGCACTTAACTTAATGAGTGTGATCAACCCTAACATCACGCATTCTATGATTGATGGT
GCAGTGTTCCGTGAAGAATCTGAAAACATCATGGCAGTCCCTGCTGTCTTTTTAAATGGCGAAGAATTTGGCAATGG
TCGTATGACAATCCAAGATATTCTTTCGAAACTAGGCAGTACGGCAGATGCATCTGAGTTTGAAAATAAAGAACCTT
ATGATGTCTTAATCGTTGGTGGTGGTCCTGCTAGTGGTAGTGCAGCGATTTACACAGCACGTAAAGGTTTACGTACT
GGTATAGTTGCTGATCGTATCGGTGGCCAAGTTAATGATACTGCTGGTATTGAGAACTTCATTACTGTTAAAGAAAC
AACTGGTTCTGAATTTTCTTCTAACTTAGCAGCGCACATTGATCAATATGACATTGATGCAATGACAGGTATACGTG
CTACAGATATCGAAAAGACTGACGAAGCAATTAAAGTTACGTTAGAAAACGGTGCTGTCTTAGAAAGTAAAACAGTC
ATTATTGCTACTGGTGCAGGTTGGCGTAAGCTAAACATTCCAGGTGAAGAGCAATTGATTAATAAAGGTGTTGCATT
CTGCCCTCACTGTGACGGACCTCTATTTGAAAATAAAGACGTAGCAGTTATCGGTGGCGGTAACTCTGGGGTTGAAG
CAGCAATTGACCTTGCTGGTATCGTTAATCATGTTACATTATTCGAATTCGCTAGCGAATTAAAAGCAGACAACGTG
TTACAAGATCGTTTACGTTCTTTATCAAATGTTGATATCAAAACAAATGCCAAAACTACTGAAGTTGTCGGAGAAGA
CCATGTTACAGGTATACGTTACGAAGACATGAACACCGGCGAAGAACATCTACTTAACTTAGATGGTATCTTTGTTC
AAATTGGTTTACTTCCAAACACATCATGGTTAAACGATGCTGTTGAATTAAACGAACGTGGTGAAATTGTGATTGAT
CGTAACAATAATACGAATGTTCCTGGAATATTTGCTGCTGGCGATGTCACAGATCAGAAGAACAAACAAATTATCAT
TTCAATGGGCGCTGGTGCAAATGCAGCATTAAATGCCTTGACTATATTATCAGAAAC (SEQ ID NO: 4)
```

FIG. 4

```
                    1                                                  50
SEQ ID NO:  8  MLNADLKQQLQQLLELMEGDVEFVASLGSDDKSNELKELLNEIAEMSAHI
SEQ ID NO:  3  MLNADLKQQLKQLLELMEGNVEFVASLGSDDKSKELKDLLTEITDMSPRL
SEQ ID NO:  9  MLNADLKQQLKQLLELMEGNVEFVASLGSDEKSKELKELLTEISDMSPRL
SEQ ID NO: 10  MLNADLKQQLKQLLELMEGNVEFVASLGSDEKSKELKELLTEISDMSPRL 51                                                 100
SEQ ID NO:  8  TITEKSLKRTPSFSVNRPGEETGITFAGIPLGHEFNSLVLAILQVSGRAP
SEQ ID NO:  3  SLSEKSLKRTPSFSVNRPGEETGVTFAGIPLGHEFNSLVLAILQVSGRAP
SEQ ID NO:  9  SLSEKSLKRTPSFSVNRPGEETGVTFAGIPLGHEFNSLVLAILQVSGRAP
SEQ ID NO: 10  SLSEKSLKRTPSFSVNRPGEETGVTFAGIPLGHEFNSLVLAILQVSGRAP 101                                                 150
SEQ ID NO:  8  KEKQSIIDQIKGLEGPFHFETFVSLTCQKCPDVVQALNLMSVINPNITHT
SEQ ID NO:  3  KEKQSIIDQIKKLEGSFHFETFISLTCQKCPDVVQALNLMSVINPNITHS
SEQ ID NO:  9  KEKQSIIDQIKNLEGSFHFETFISLTCQKCPDVVQALNLMSVINPNITHS
SEQ ID NO: 10  KEKQSIIDQIKNLEGSFHFETFISLTCQKCPDVVQALNLMSVINPNITHS 151                                                 200
SEQ ID NO:  8  MIDGAVFREESENIMAVPAVFLDGQEFGNGRMTVQDILTKLGSTQDASEF
SEQ ID NO:  3  MIDGAVFREESENIMAVPAVFLNGEEFGNGRMTIQDILSKLGSTADASEF
SEQ ID NO:  9  MIDGAVFREESENIMAVPAVFLNGEEFGNGRMTIQDILSKLGSTADASEF
SEQ ID NO: 10  MIDGAVFREESENIMAVPAVFLNGEEFGNGRMTIQDILSKLGSTADASEF
```

FIG. 5A

```
              201                                                    250
SEQ ID NO:  8 NDKDPYDVLIVGGGPASGSAAIYTARKGLRTGIVADRIGGQVNDTAGIEN
SEQ ID NO:  3 ENKEPYDVLIVGGGPASGSAAIYTARKGLRTGIVADRIGGQVNDTAGIEN
SEQ ID NO:  9 ENKEPYDVLIVGGGPASGSAAIYTARKGLRTGIVADRIGGQVNDTAGIEN
SEQ ID NO: 10 ENKEPYDVLIVGGGPASGSAAIYTARKGLRTGIVADRIGGQVNDTAGIEN 251                                                    300
SEQ ID NO:  8 FITVKETTGSEFSSNLAEHIAQYDIDTMTGIRATNIEKTDSAIRVTLEND
SEQ ID NO:  3 FITVKETTGSEFSSNLAAHIDQYDIDAMTGIRATDIEKTDEAIKVTLENG
SEQ ID NO:  9 FITVKETTGSEFSSNLAAHIDQYDIDAMTGIRATDIEKTDEAIKVTLENG
SEQ ID NO: 10 FITVKETTGSEFSSNLAAHIDQYDIDAMTGIRATDIEKTDEAIKVTLENG 301                                                    350
SEQ ID NO:  8 AVLESKTVIISTGASWRKLNIPGEDRLINKGVAFCPHCDGPLFENKDVAV
SEQ ID NO:  3 AVLESKTVIIATGAGWRKLNIPGEEQLINKGVAFCPHCDGPLFENKDVAV
SEQ ID NO:  9 AVLESKTVIIATGAGWRKLNIPGEEQLINKGVAFCPHCDGPLFENKDVAV
SEQ ID NO: 10 AVLESKTVIIATGAGWRKLNIPGEEQLINKGVAFCPHCDGPLFENKDVAV 351                                                    400
SEQ ID NO:  8 IGGGNSGVEAAIDLAGIVKHVTLFEYASELKADSVLQERLRSLPNVDIKT
SEQ ID NO:  3 IGGGNSGVEAAIDLAGIVNHVTLFEFASELKADNVLQDRLRSLSNVDIKT
SEQ ID NO:  9 IGGGNSGVEAAIDLAGIVNHVTLFEFASELKADNVLQDRLRSLSNVDIKT
SEQ ID NO: 10 IGGGNSGVEAAIDLAGIVNHVTLFEFASELKADNVLQDRLRSLSNVDIKT 401                                                    450
SEQ ID NO:  8 SAKTTEVIGDDYVTGISYEDMTTGESQVVNLDGIFVQIGLVPNTSWLQNA
SEQ ID NO:  3 NAKTTEVVGEDHVTGIRYEDMNTGEEHLLNLDGIFVQIGLLPNTSWLNDA
SEQ ID NO:  9 NAKTTEVVGEDHVTGIRYEDMSTGEEHLLNLDGIFVQIGLLPNTSWLKDA
SEQ ID NO: 10 NAKTTEVVGEDHVTGIRYEDMSTGEEHLLNLDGIFVQIGLLPNTSWLKDA 451                                                    500
SEQ ID NO:  8 VELNERGEVMINRDNATNVPGIFAAGDVTDQKNKQIIISMGAGANAALNA
SEQ ID NO:  3 VELNERGEIVIDRNNNTNVPGIFAAGDVTDQKNKQIIISMGAGANAALNA
SEQ ID NO:  9 VELNERGEIVIDRNNNTNVPGIFAAGDVTDQKNKQIIISMGAGANAALNA
SEQ ID NO: 10 VELNERGEIVIDCNNNTNVPGIFAAGDVTDQKNKQIIISMGAGANAALNA

501
SEQ ID NO:  8 FDYIIRN
SEQ ID NO:  3 FDYIIRN
SEQ ID NO:  9 FDYIIRN
SEQ ID NO: 10 FDYIIRN
```

FIG. 5B

SEQUENCE LISTING

```
<160> NUMBER OF SEQ ID NOS: 11

<210> SEQ ID NO 1
<211> LENGTH: 189
<212> TYPE: PRT
<213> ORGANISM: S. aureus

<400> SEQUENCE: 1

Met Ser Leu Ile Asn Lys Glu Ile Leu Pro Phe Thr Ala Gln Ala Phe
 1               5                  10                  15

Asp Pro Lys Lys Asp Gln Phe Lys Glu Val Thr Gln Glu Asp Leu Lys
            20                  25                  30

Gly Ser Trp Ser Val Val Cys Phe Tyr Pro Ala Asp Phe Ser Phe Val
        35                  40                  45

Cys Pro Thr Glu Leu Glu Asp Leu Gln Asn Gln Tyr Glu Glu Leu Gln
    50                  55                  60

Lys Leu Gly Val Asn Val Phe Ser Val Ser Thr Asp Thr His Phe Val
65                  70                  75                  80

His Lys Ala Trp His Asp His Ser Asp Ala Ile Ser Lys Ile Thr Tyr
                85                  90                  95

Thr Met Ile Gly Asp Pro Ser Gln Thr Ile Thr Arg Asn Phe Asp Val
            100                 105                 110

Leu Asp Glu Ala Thr Gly Leu Ala Gln Arg Gly Thr Phe Ile Ile Asp
        115                 120                 125

Pro Asp Gly Val Val Gln Ala Ser Glu Ile Asn Ala Asp Gly Ile Gly
    130                 135                 140
```

```
Arg Asp Ala Ser Thr Leu Ala His Lys Ile Lys Ala Ala Gln Tyr Val
145                 150                 155                 160

Arg Lys Asn Pro Gly Glu Val Cys Pro Ala Lys Trp Glu Gly Ala
                165                 170                 175

Lys Thr Leu Gln Pro Gly Leu Asp Leu Val Gly Lys Ile
            180                 185

<210> SEQ ID NO 2
<211> LENGTH: 213
<212> TYPE: PRT
<213> ORGANISM: Artificial Sequence
<220> FEATURE:
<223> OTHER INFORMATION: His-tagged derivative of SEQ ID NO: 1

<400> SEQUENCE: 2

Met Gly His His His His His His His His Ser Ser Gly His
 1               5                  10                  15

Ile Glu Gly Arg His Met Ser Leu Ile Asn Lys Glu Ile Leu Pro Phe
                20                  25                  30

Thr Ala Gln Ala Phe Asp Pro Lys Lys Asp Gln Phe Lys Glu Val Thr
            35                  40                  45

Gln Glu Asp Leu Lys Gly Ser Trp Ser Val Val Cys Phe Tyr Pro Ala
50                  55                  60

Asp Phe Ser Phe Val Cys Pro Thr Glu Leu Glu Asp Leu Gln Asn Gln
65                  70                  75                  80

Tyr Glu Glu Leu Gln Lys Leu Gly Val Asn Val Phe Ser Val Ser Thr
                85                  90                  95

Asp Thr His Phe Val His Lys Ala Trp His Asp His Ser Asp Ala Ile
            100                 105                 110

Ser Lys Ile Thr Tyr Thr Met Ile Gly Asp Pro Ser Gln Thr Ile Thr
        115                 120                 125

Arg Asn Phe Asp Val Leu Asp Glu Ala Thr Gly Leu Ala Gln Arg Gly
    130                 135                 140

Thr Phe Ile Ile Asp Pro Asp Gly Val Val Gln Ala Ser Glu Ile Asn
145                 150                 155                 160

Ala Asp Gly Ile Gly Arg Asp Ala Ser Thr Leu Ala His Lys Ile Lys
                165                 170                 175

Ala Ala Gln Tyr Val Arg Lys Asn Pro Gly Glu Val Cys Pro Ala Lys
            180                 185                 190

Trp Glu Glu Gly Ala Lys Thr Leu Gln Pro Gly Leu Asp Leu Val Gly
        195                 200                 205

Lys Ile Ala Glu Gln
    210

<210> SEQ ID NO 3
<211> LENGTH: 507
<212> TYPE: PRT
<213> ORGANISM: S. aureus

<400> SEQUENCE: 3

Met Leu Asn Ala Asp Leu Lys Gln Gln Leu Lys Gln Leu Leu Glu Leu
 1               5                  10                  15

Met Glu Gly Asn Val Glu Phe Val Ala Ser Leu Gly Ser Asp Asp Lys
                20                  25                  30

Ser Lys Glu Leu Lys Asp Leu Leu Thr Glu Ile Thr Asp Met Ser Pro
        35                  40                  45
```

-continued

```
Arg Leu Ser Leu Ser Glu Lys Ser Leu Lys Arg Thr Pro Ser Phe Ser
 50                  55                  60

Val Asn Arg Pro Gly Glu Glu Thr Gly Val Thr Phe Ala Gly Ile Pro
 65                  70                  75                  80

Leu Gly His Glu Phe Asn Ser Leu Val Leu Ala Ile Leu Gln Val Ser
                 85                  90                  95

Gly Arg Ala Pro Lys Glu Lys Gln Ser Ile Ile Asp Gln Ile Lys Lys
                100                 105                 110

Leu Glu Gly Ser Phe His Phe Glu Thr Phe Ile Ser Leu Thr Cys Gln
                115                 120                 125

Lys Cys Pro Asp Val Val Gln Ala Leu Asn Leu Met Ser Val Ile Asn
130                 135                 140

Pro Asn Ile Thr His Ser Met Ile Asp Gly Ala Val Phe Arg Glu Glu
145                 150                 155                 160

Ser Glu Asn Ile Met Ala Val Pro Ala Val Phe Leu Asn Gly Glu Glu
                165                 170                 175

Phe Gly Asn Gly Arg Met Thr Ile Gln Asp Ile Leu Ser Lys Leu Gly
                180                 185                 190

Ser Thr Ala Asp Ala Ser Glu Phe Glu Asn Lys Glu Pro Tyr Asp Val
                195                 200                 205

Leu Ile Val Gly Gly Gly Pro Ala Ser Gly Ser Ala Ala Ile Tyr Thr
210                 215                 220

Ala Arg Lys Gly Leu Arg Thr Gly Ile Val Ala Asp Arg Ile Gly Gly
225                 230                 235                 240

Gln Val Asn Asp Thr Ala Gly Ile Glu Asn Phe Ile Thr Val Lys Glu
                245                 250                 255

Thr Thr Gly Ser Glu Phe Ser Ser Asn Leu Ala Ala His Ile Asp Gln
                260                 265                 270

Tyr Asp Ile Asp Ala Met Thr Gly Ile Arg Ala Thr Asp Ile Glu Lys
                275                 280                 285

Thr Asp Glu Ala Ile Lys Val Thr Leu Glu Asn Gly Ala Val Leu Glu
290                 295                 300

Ser Lys Thr Val Ile Ile Ala Thr Gly Ala Gly Trp Arg Lys Leu Asn
305                 310                 315                 320

Ile Pro Gly Glu Glu Gln Leu Ile Asn Lys Gly Val Ala Phe Cys Pro
                325                 330                 335

His Cys Asp Gly Pro Leu Phe Glu Asn Lys Asp Val Ala Val Ile Gly
                340                 345                 350

Gly Gly Asn Ser Gly Val Glu Ala Ala Ile Asp Leu Ala Gly Ile Val
                355                 360                 365

Asn His Val Thr Leu Phe Glu Phe Ala Ser Glu Leu Lys Ala Asp Asn
370                 375                 380

Val Leu Gln Asp Arg Leu Arg Ser Leu Ser Asn Val Asp Ile Lys Thr
385                 390                 395                 400

Asn Ala Lys Thr Thr Glu Val Val Gly Glu Asp His Val Thr Gly Ile
                405                 410                 415

Arg Tyr Glu Asp Met Asn Thr Gly Glu Glu His Leu Leu Asn Leu Asp
                420                 425                 430

Gly Ile Phe Val Gln Ile Gly Leu Leu Pro Asn Thr Ser Trp Leu Asn
                435                 440                 445

Asp Ala Val Glu Leu Asn Glu Arg Gly Glu Ile Val Ile Asp Arg Asn
450                 455                 460
```

```
Asn Asn Thr Asn Val Pro Gly Ile Phe Ala Ala Gly Asp Val Thr Asp
465                 470                 475                 480

Gln Lys Asn Lys Gln Ile Ile Ile Ser Met Gly Ala Gly Ala Asn Ala
                485                 490                 495

Ala Leu Asn Ala Phe Asp Tyr Ile Ile Arg Asn
            500                 505

<210> SEQ ID NO 4
<211> LENGTH: 1521
<212> TYPE: DNA
<213> ORGANISM: Artificial Sequence
<220> FEATURE:
<223> OTHER INFORMATION: DNA sequence encoding for SEQ ID NO: 3

<400> SEQUENCE: 4
atgcttaatg ctgatttaaa acaacaactt aaacaactat tagaactaat ggagggcaac    60
gttgaattcg ttgccagcct tggttcagat gataaatcca agaacttaa agatttgttg     120 acagaaatta ctgatatgtc acctagacta tctctttctg aaaaatcttt aaaacgtaca    180
ccaagtttct cagtcaatcg tcctggcgaa gaaacaggtg taacatttgc aggtattcca    240
ttaggtcacg agtttaactc acttgtttta gcaattttac aggttagtgg tcgtgcacct    300
aaagaaaaac agtcaatcat tgaccaaatt aaaaaattag aaggttcatt ccatttgaa    360 acattcatta gtttaacgtg tcaaaaatgt cctgatgtcg ttcaagcact taacttaatg    420
agtgtgatca accctaacat cacgcattct atgattgatg gtgcagtgtt ccgtgaagaa    480
tctgaaaaca tcatggcagt ccctgctgtc ttttaaatg gcgaagaatt tggcaatggt    540
cgtatgacaa tccaagatat tctttcgaaa ctaggcagta cggcagatgc atctgagttt    600
gaaaataaag aaccttatga tgtcttaatc gttggtggtg tcctgctag tggtagtgca    660 gcgatttaca cagcacgtaa aggtttacgt actggtatag ttgctgatcg tatcggtggc    720
caagttaatg atactgctgg tattgagaac ttcattactg ttaaagaaac aactggttct    780
gaattttctt ctaacttagc agcgcacatt gatcaatatg acattgatgc aatgacaggt    840
atacgtgcta cagatatcga aaagactgac gaagcaatta agttacgtt agaaaacggt    900 gctgtcttag aaagtaaaac agtcattatt gctactggtg caggttggcg taagctaaac    960
attccaggtg aagagcaatt gattaataaa ggtgttgcat tctgccctca ctgtgacgga   1020
cctctatttg aaaataaaga cgtagcagtt atcggtggcg gtaactctgg ggttgaagca   1080
gcaattgacc ttgctggtat cgttaatcat gttacattat tcgaattcgc tagcgaatta   1140
aaagcagaca acgtgttaca agatcgttta cgttctttat caaatgttga tatcaaaaca   1200
aatgccaaaa ctactgaagt tgtcggagaa gaccatgtta caggtatacg ttacgaagac   1260
atgaacaccg gcgaagaaca tctacttaac ttagatggta tctttgttca aattggttta   1320
cttccaaaca catcatggtt aaacgatgct gttgaattaa acgaacgtgg tgaaattgtg   1380
attgatcgta caataatac gaatgttcct ggaatatttg ctgctggcga tgtcacagat   1440
cagaagaaca aacaaattat catttcaatg ggcgctggtg caaatgcagc attaaatgcc   1500
tttgactata ttatcagaaa c                                              1521

<210> SEQ ID NO 5
<211> LENGTH: 642
<212> TYPE: DNA
<213> ORGANISM: Artificial Sequence
<220> FEATURE:
<223> OTHER INFORMATION: nucleic acid sequence encoding SEQ ID NO: 2
```

<400> SEQUENCE: 5

```
atgggccatc atcatcatca tcatcatcat catcacagca gcggccatat cgaaggtcgt    60
catatgtcat taattaacaa agaaatctta ccatttacag cgcaagcttt cgatccaaaa   120
aaagatcaat ttaaagaagt tacacaagaa gatttaaaag gttcttggag cgtagtatgc   180
ttctatcctg ctgacttctc attcgtttgt ccaactgaat tagaagactt acaaaaccaa   240
tatgaagaat tacaaaaatt aggcgtaaat gtattctcag tatcaactga tactcacttc   300
gtacacaaag catggcatga ccattcagat gcaattagca aaatcactta cactatgatt   360
ggtgacccat cacaaacaat cactcgtaat tttgatgtat tagatgaagc tactggttta   420
gctcaacgtg gtacattcat tatcgaccca gacggtgttg tacaagcatc tgaaattaac   480
gctgacggaa ttggccgtga cgctagtaca ttagctcaca aaatcaaagc agctcaatat   540
gttcgtaaaa accctggcga agtatgccca gctaaatggg aagaaggcgc taaaacattg   600
caacctggtt tagatttagt aggtaaaatc gctgagcaat aa                     642
```

<210> SEQ ID NO 6
<211> LENGTH: 189
<212> TYPE: PRT
<213> ORGANISM: S. epidermidis

<400> SEQUENCE: 6

```
Met Ser Leu Ile Asn Lys Glu Ile Leu Pro Phe Thr Ala Gln Ala Tyr
1               5                   10                  15

Asp Pro Lys Lys Asp Glu Phe Lys Glu Val Thr Gln Glu Asp Phe Lys
            20                  25                  30

Gly Ser Trp Asn Val Val Cys Phe Tyr Pro Ala Asp Phe Ser Phe Val
        35                  40                  45

Cys Pro Thr Glu Leu Glu Asp Leu Gln Asn Gln Tyr Ala Lys Leu Gln
    50                  55                  60

Glu Leu Gly Val Asn Val Tyr Ser Val Ser Thr Asp Thr His Phe Val
65                  70                  75                  80

His Lys Ala Trp His Asp His Ser Asp Ala Ile Ser Lys Leu Glu Tyr
                85                  90                  95

Ser Met Ile Gly Asp Pro Ser Gln Thr Ile Thr Arg Asn Phe Asp Val
            100                 105                 110

Leu Asp Glu Glu Thr Gly Leu Ala Gln Arg Gly Thr Phe Ile Ile Asp
        115                 120                 125

Pro Asp Gly Val Val Gln Ala Ala Glu Ile Asn Ala Asp Gly Ile Gly
    130                 135                 140

Arg Asp Ala Ser Thr Leu Val Asn Lys Ile Lys Ala Ala Gln Tyr Val
145                 150                 155                 160

Arg Gln His Pro Gly Glu Val Cys Pro Ala Lys Trp Glu Glu Gly Ser
                165                 170                 175

Glu Ser Leu Gln Pro Gly Leu Asp Leu Val Gly Lys Ile
            180                 185
```

<210> SEQ ID NO 7
<211> LENGTH: 40
<212> TYPE: DNA
<213> ORGANISM: Artificial Sequence
<220> FEATURE:
<223> OTHER INFORMATION: PCR primer

<400> SEQUENCE: 7

```
gggaattcca tatgtcatta attaacaaag aaatcttacc                          40
```

<210> SEQ ID NO 8
<211> LENGTH: 507
<212> TYPE: PRT
<213> ORGANISM: s. epidermidis

<400> SEQUENCE: 8

```
Met Leu Asn Ala Asp Leu Lys Gln Gln Leu Gln Gln Leu Leu Glu Leu
1               5                   10                  15

Met Glu Gly Asp Val Glu Phe Val Ala Ser Leu Gly Ser Asp Asp Lys
            20                  25                  30

Ser Asn Glu Leu Lys Glu Leu Leu Asn Glu Ile Ala Glu Met Ser Ala
        35                  40                  45

His Ile Thr Ile Thr Glu Lys Ser Leu Lys Arg Thr Pro Ser Phe Ser
    50                  55                  60

Val Asn Arg Pro Gly Glu Thr Gly Ile Thr Phe Ala Gly Ile Pro
65                  70                  75                  80

Leu Gly His Glu Phe Asn Ser Leu Val Leu Ala Ile Leu Gln Val Ser
                85                  90                  95

Gly Arg Ala Pro Lys Glu Lys Gln Ser Ile Ile Asp Gln Ile Lys Gly
            100                 105                 110

Leu Glu Gly Pro Phe His Phe Glu Thr Phe Val Ser Leu Thr Cys Gln
        115                 120                 125

Lys Cys Pro Asp Val Val Gln Ala Leu Asn Leu Met Ser Val Ile Asn
    130                 135                 140

Pro Asn Ile Thr His Thr Met Ile Asp Gly Ala Val Phe Arg Glu Glu
145                 150                 155                 160

Ser Glu Asn Ile Met Ala Val Pro Ala Val Phe Leu Asp Gly Gln Glu
                165                 170                 175

Phe Gly Asn Gly Arg Met Thr Val Gln Asp Ile Leu Thr Lys Leu Gly
            180                 185                 190

Ser Thr Gln Asp Ala Ser Glu Phe Asn Asp Lys Asp Pro Tyr Asp Val
        195                 200                 205

Leu Ile Val Gly Gly Pro Ala Ser Gly Ser Ala Ala Ile Tyr Thr
    210                 215                 220

Ala Arg Lys Gly Leu Arg Thr Gly Ile Val Ala Asp Arg Ile Gly Gly
225                 230                 235                 240

Gln Val Asn Asp Thr Ala Gly Ile Glu Asn Phe Ile Thr Val Lys Glu
                245                 250                 255

Thr Thr Gly Ser Glu Phe Ser Ser Asn Leu Ala Glu His Ile Ala Gln
            260                 265                 270

Tyr Asp Ile Asp Thr Met Thr Gly Ile Arg Ala Thr Asn Ile Glu Lys
        275                 280                 285

Thr Asp Ser Ala Ile Arg Val Thr Leu Glu Asn Asp Ala Val Leu Glu
    290                 295                 300

Ser Lys Thr Val Ile Ile Ser Thr Gly Ala Ser Trp Arg Lys Leu Asn
305                 310                 315                 320

Ile Pro Gly Glu Asp Arg Leu Ile Asn Lys Gly Val Ala Phe Cys Pro
                325                 330                 335

His Cys Asp Gly Pro Leu Phe Glu Asn Lys Asp Val Ala Val Ile Gly
            340                 345                 350

Gly Gly Asn Ser Gly Val Glu Ala Ala Ile Asp Leu Ala Gly Ile Val
        355                 360                 365
```

```
Lys His Val Thr Leu Phe Glu Tyr Ala Ser Glu Leu Lys Ala Asp Ser
        370                 375                 380

Val Leu Gln Glu Arg Leu Arg Ser Leu Pro Asn Val Asp Ile Lys Thr
385                 390                 395                 400

Ser Ala Lys Thr Thr Glu Val Ile Gly Asp Asp Tyr Val Thr Gly Ile
                405                 410                 415

Ser Tyr Glu Asp Met Thr Thr Gly Glu Ser Gln Val Val Asn Leu Asp
                420                 425                 430

Gly Ile Phe Val Gln Ile Gly Leu Val Pro Asn Thr Ser Trp Leu Gln
                435                 440                 445

Asn Ala Val Glu Leu Asn Glu Arg Gly Glu Val Met Ile Asn Arg Asp
        450                 455                 460

Asn Ala Thr Asn Val Pro Gly Ile Phe Ala Ala Gly Asp Val Thr Asp
465                 470                 475                 480

Gln Lys Asn Lys Gln Ile Ile Ile Ser Met Gly Ala Gly Ala Asn Ala
                485                 490                 495

Ala Leu Asn Ala Phe Asp Tyr Ile Ile Arg Asn
                500                 505

<210> SEQ ID NO 9
<211> LENGTH: 507
<212> TYPE: PRT
<213> ORGANISM: S. aureus

<400> SEQUENCE: 9

Met Leu Asn Ala Asp Leu Lys Gln Gln Leu Lys Gln Leu Leu Glu Leu
1               5                   10                  15

Met Glu Gly Asn Val Glu Phe Val Ala Ser Leu Gly Ser Asp Glu Lys
                20                  25                  30

Ser Lys Glu Leu Lys Glu Leu Leu Thr Glu Ile Ser Asp Met Ser Pro
            35                  40                  45

Arg Leu Ser Leu Ser Glu Lys Ser Leu Lys Arg Thr Pro Ser Phe Ser
        50                  55                  60

Val Asn Arg Pro Gly Glu Glu Thr Gly Val Thr Phe Ala Gly Ile Pro
65                  70                  75                  80

Leu Gly His Glu Phe Asn Ser Leu Val Leu Ala Ile Leu Gln Val Ser
                85                  90                  95

Gly Arg Ala Pro Lys Glu Lys Gln Ser Ile Ile Asp Gln Ile Lys Asn
                100                 105                 110

Leu Glu Gly Ser Phe His Phe Glu Thr Phe Ile Ser Leu Thr Cys Gln
            115                 120                 125

Lys Cys Pro Asp Val Val Gln Ala Leu Asn Leu Met Ser Val Ile Asn
130                 135                 140

Pro Asn Ile Thr His Ser Met Ile Asp Gly Ala Val Phe Arg Glu Glu
145                 150                 155                 160

Ser Glu Asn Ile Met Ala Val Pro Ala Val Phe Leu Asn Gly Glu Glu
                165                 170                 175

Phe Gly Asn Gly Arg Met Thr Ile Gln Asp Ile Leu Ser Lys Leu Gly
                180                 185                 190

Ser Thr Ala Asp Ala Ser Glu Phe Glu Asn Lys Glu Pro Tyr Asp Val
            195                 200                 205

Leu Ile Val Gly Gly Gly Pro Ala Gly Ser Ala Ala Ile Tyr Thr
        210                 215                 220

Ala Arg Lys Gly Leu Arg Thr Gly Ile Val Ala Asp Arg Ile Gly Gly
225                 230                 235                 240
```

```
Gln Val Asn Asp Thr Ala Gly Ile Glu Asn Phe Ile Thr Val Lys Glu
                245                 250                 255

Thr Thr Gly Ser Glu Phe Ser Ser Asn Leu Ala Ala His Ile Asp Gln
            260                 265                 270

Tyr Asp Ile Asp Ala Met Thr Gly Ile Arg Ala Thr Asp Ile Glu Lys
        275                 280                 285

Thr Asp Glu Ala Ile Lys Val Thr Leu Glu Asn Gly Ala Val Leu Glu
    290                 295                 300

Ser Lys Thr Val Ile Ile Ala Thr Gly Ala Gly Trp Arg Lys Leu Asn
305                 310                 315                 320

Ile Pro Gly Glu Glu Gln Leu Ile Asn Lys Gly Val Ala Phe Cys Pro
                325                 330                 335

His Cys Asp Gly Pro Leu Phe Glu Asn Lys Asp Val Ala Val Ile Gly
            340                 345                 350

Gly Gly Asn Ser Gly Val Glu Ala Ala Ile Asp Leu Ala Gly Ile Val
        355                 360                 365

Asn His Val Thr Leu Phe Glu Phe Ala Ser Glu Leu Lys Ala Asp Asn
    370                 375                 380

Val Leu Gln Asp Arg Leu Arg Ser Leu Ser Asn Val Asp Ile Lys Thr
385                 390                 395                 400

Asn Ala Lys Thr Thr Glu Val Val Gly Glu Asp His Val Thr Gly Ile
                405                 410                 415

Arg Tyr Glu Asp Met Ser Thr Gly Glu Glu His Leu Leu Asn Leu Asp
            420                 425                 430

Gly Ile Phe Val Gln Ile Gly Leu Leu Pro Asn Thr Ser Trp Leu Lys
        435                 440                 445

Asp Ala Val Glu Leu Asn Glu Arg Gly Glu Ile Val Ile Asp Arg Asn
    450                 455                 460

Asn Asn Thr Asn Val Pro Gly Ile Phe Ala Ala Gly Asp Val Thr Asp
465                 470                 475                 480

Gln Lys Asn Lys Gln Ile Ile Ile Ser Met Gly Ala Gly Ala Asn Ala
                485                 490                 495

Ala Leu Asn Ala Phe Asp Tyr Ile Ile Arg Asn
            500                 505

<210> SEQ ID NO 10
<211> LENGTH: 507
<212> TYPE: PRT
<213> ORGANISM: S. aureus

<400> SEQUENCE: 10

Met Leu Asn Ala Asp Leu Lys Gln Gln Leu Lys Gln Leu Leu Glu Leu
1               5                   10                  15

Met Glu Gly Asn Val Glu Phe Val Ala Ser Leu Gly Ser Asp Glu Lys
            20                  25                  30

Ser Lys Glu Leu Lys Glu Leu Leu Thr Glu Ile Ser Asp Met Ser Pro
        35                  40                  45

Arg Leu Ser Leu Ser Glu Lys Ser Leu Lys Arg Thr Pro Ser Phe Ser
    50                  55                  60

Val Asn Arg Pro Gly Glu Glu Thr Gly Val Thr Phe Ala Gly Ile Pro
65                  70                  75                  80

Leu Gly His Glu Phe Asn Ser Leu Val Leu Ala Ile Leu Gln Val Ser
                85                  90                  95
```

-continued

```
Gly Arg Ala Pro Lys Glu Lys Gln Ser Ile Ile Asp Gln Ile Lys Asn
            100                 105                 110

Leu Glu Gly Ser Phe His Phe Glu Thr Phe Ile Ser Leu Thr Cys Gln
        115                 120                 125

Lys Cys Pro Asp Val Val Gln Ala Leu Asn Leu Met Ser Val Ile Asn
    130                 135                 140

Pro Asn Ile Thr His Ser Met Ile Asp Gly Ala Val Phe Arg Glu Glu
145                 150                 155                 160

Ser Glu Asn Ile Met Ala Val Pro Ala Val Phe Leu Asn Gly Glu Glu
                165                 170                 175

Phe Gly Asn Gly Arg Met Thr Ile Gln Asp Ile Leu Ser Lys Leu Gly
            180                 185                 190

Ser Thr Ala Asp Ala Ser Glu Phe Glu Asn Lys Glu Pro Tyr Asp Val
        195                 200                 205

Leu Ile Val Gly Gly Gly Pro Ala Ser Gly Ser Ala Ala Ile Tyr Thr
    210                 215                 220

Ala Arg Lys Gly Leu Arg Thr Gly Ile Val Ala Asp Arg Ile Gly Gly
225                 230                 235                 240

Gln Val Asn Asp Thr Ala Gly Ile Glu Asn Phe Ile Thr Val Lys Glu
                245                 250                 255

Thr Thr Gly Ser Glu Phe Ser Ser Asn Leu Ala Ala His Ile Asp Gln
            260                 265                 270

Tyr Asp Ile Asp Ala Met Thr Gly Ile Arg Ala Thr Asp Ile Glu Lys
        275                 280                 285

Thr Asp Glu Ala Ile Lys Val Thr Leu Glu Asn Gly Ala Val Leu Glu
    290                 295                 300

Ser Lys Thr Val Ile Ile Ala Thr Gly Ala Gly Trp Arg Lys Leu Asn
305                 310                 315                 320

Ile Pro Gly Glu Glu Gln Leu Ile Asn Lys Gly Val Ala Phe Cys Pro
                325                 330                 335

His Cys Asp Gly Pro Leu Phe Glu Asn Lys Asp Val Ala Val Ile Gly
            340                 345                 350

Gly Gly Asn Ser Gly Val Glu Ala Ala Ile Asp Leu Ala Gly Ile Val
        355                 360                 365

Asn His Val Thr Leu Phe Glu Phe Ala Ser Glu Leu Lys Ala Asp Asn
    370                 375                 380

Val Leu Gln Asp Arg Leu Arg Ser Leu Ser Asn Val Asp Ile Lys Thr
385                 390                 395                 400

Asn Ala Lys Thr Thr Glu Val Val Gly Glu Asp His Val Thr Gly Ile
                405                 410                 415

Arg Tyr Glu Asp Met Ser Thr Gly Glu Glu His Leu Leu Asn Leu Asp
            420                 425                 430

Gly Ile Phe Val Gln Ile Gly Leu Leu Pro Asn Thr Ser Trp Leu Lys
        435                 440                 445

Asp Ala Val Glu Leu Asn Glu Arg Gly Glu Ile Val Ile Asp Cys Asn
    450                 455                 460

Asn Asn Thr Asn Val Pro Gly Ile Phe Ala Ala Gly Asp Val Thr Asp
465                 470                 475                 480

Gln Lys Asn Lys Gln Ile Ile Ile Ser Met Gly Ala Gly Ala Asn Ala
                485                 490                 495

Ala Leu Asn Ala Phe Asp Tyr Ile Ile Arg Asn
            500                 505
```

-continued

```
<210> SEQ ID NO 11
<211> LENGTH: 35
<212> TYPE: DNA
<213> ORGANISM: Artificial Sequence
<220> FEATURE:
<223> OTHER INFORMATION: PCR primer

<400> SEQUENCE: 11
gggctcagcg attttaccta ctaaatctaa accag                              35
```

POLYPEPTIDES FOR INDUCING A PROTECTIVE IMMUNE RESPONSE AGAINST *STAPHYLOCOCCUS AUREUS*

CROSS-REFERENCE TO RELATED APPLICATIONS

The present application claims the benefit of U.S. Provisional Application No. 60/645,811 filed Jan. 21, 2005, which is hereby incorporated by reference herein.

BACKGROUND OF THE INVENTION

The references cited throughout the present application are not admitted to be prior art to the claimed invention.

*Staphylococcus aureus* is a pathogen responsible for a wide range of diseases and conditions. Examples of diseases and conditions caused by *S. aureus* include bacteremia, infective endocarditis, folliculitis, furuncle, carbuncle, impetigo, bullous impetigo, cellulitis, botryomyosis, toxic shock syndrome, scalded skin syndrome, central nervous system infections, infective and inflammatory eye disease, osteomyelitis and other infections of joints and bones, and respiratory tract infections. (*The Staphylococci in Human Disease*, Crossley and Archer (eds.), Churchill Livingstone Inc. 1997.)

Immunological based strategies can be employed to control *S. aureus* infections and the spread of *S. aureus*. Immunological based strategies include passive and active immunization. Passive immunization employs immunoglobulins targeting *S. aureus*. Active immunization induces immune responses against *S. aureus*.

Potential *S. aureus* vaccines target *S. aureus* polysaccharides and polypeptides. Targeting can be achieved using suitable *S. aureus* polysaccharides or polypeptides as vaccine components. Examples of polysaccharides that may be employed as possible vaccine components include *S. aureus* type 5 and type 8 capsular polysaccharides. (Shinefield et al., *N. Eng. J. Med.* 346:491-496, 2002.) Examples of polypeptides that may be employed as possible vaccine components include collagen adhesin, fibrinogen binding proteins, and clumping factor. (Mamo et al., *FEMS Immunology and Medical Microbiology* 10:47-54, 1994, Nilsson et al., *J. Clin. Invest.* 101:2640-2649, 1998, Josefsson et al., *The Journal of Infectious Diseases* 184:1572-1580, 2001.)

Information concerning *S. aureus* polypeptide sequences has been obtained from sequencing the *S. aureus* genome. (Kuroda et al., *Lancet* 357:1225-1240, 2001, Baba et al., *Lancet* 359:1819-1827, 2000, Kunsch et al., European Patent Publication EP 0 786 519, published Jul. 30, 1997.) To some extent bioinformatics has been employed in efforts to characterize polypeptide sequences obtained from genome sequencing. (Kunsch et al., European Patent Publication EP 0 786 519, published Jul. 30, 1997.)

Techniques such as those involving display technology and sera from infected patients have been used in an effort to help identify genes coding for potential antigens. (Foster et al., International Publication Number WO 01/98499, published Dec. 27, 2001, Meinke et al., International Publication Number WO 02/059148, published Aug. 1, 2002, Etz et al., *PNAS* 99:6573-6578, 2002.)

SUMMARY OF THE INVENTION

The present invention features polypeptides comprising an amino acid sequence structurally related to SEQ ID NO: 1 or a fragment thereof, *S. aureus* AhpC-AhpF compositions, and uses of such polypeptides and compositions. SEQ ID NO: 1 has a full length *S. aureus* AhpC sequence. A derivative of SEQ ID NO: 1 containing an amino His-tag and three additional carboxyl amino acids was found to produce a protective immune response against *S. aureus*.

Reference to "protective" immunity or immune response indicates a detectable level of protection against *S. aureus* infection. The level of protection can be assessed using animal models such as those described herein.

Thus, a first aspect of the present invention describes a polypeptide immunogen comprising an amino acid sequence at least 85% identical to SEQ ID NO: 1 or to a fragment of SEQ ID NO: 1, wherein the polypeptide provides protective immunity against *S. aureus* and the polypeptide immunogen is not the polypeptide of SEQ ID NO: 1. Reference to immunogen indicates the ability to provide protective immunity against *S. aureus*.

Reference to comprising an amino acid sequence at least 85% identical to SEQ ID NO: 1 indicates that a SEQ ID NO: 1 related region is present and additional polypeptide regions may be present. Percent identity (also referred to as percent identical) to a reference sequence is determined by aligning the polypeptide sequence with the reference sequence and determining the number of identical amino acids in the corresponding regions. This number is divided by the total number of amino acids in the reference sequence (e.g., SEQ ID NO: 1) and then multiplied by 100 and rounded to the nearest whole number.

Another aspect of the present invention describes all immunogen comprising a polypeptide that provides protective immunity against *S. aureus* and one or more additional regions or moieties covalently joined to the polypeptide at the carboxyl terminus or amino terminus, wherein each region or moiety is independently selected from a region or moiety having at least one of the following properties: enhances the immune response, facilitates purification, or facilitates polypeptide stability.

Reference to "additional region or moiety" indicates a region or moiety different from a *S. aureus* AhpC region. The additional region or moiety can be, for example, an additional polypeptide region or a non-peptide region.

Another aspect of the present invention describes a purified immunogen made up of an AhpC-AhpF composition. The AhpC component comprises a polypeptide at least 85% identical to SEQ ID NO: 1. The AhpF component comprises a polypeptide at least 85% identical to SEQ ID NO: 3. Reference to purified indicates that the composition is present in an environment lacking one or more other polypeptides with which AhpC and AhpF is naturally associated and/or represents at least about 10% of the total protein present.

Preferably, the composition is substantially purified. A "substantially purified" AhpC and AhpF composition is present in an environment lacking all, or most, other polypeptides with which AhpC and AhpF polypeptide is naturally associated.

Reference to "purified" or "substantially purified" does not require a polypeptide to undergo any purification and may include, for example, a chemically synthesized polypeptide that has not been purified.

Another aspect of the present invention describes a composition able to induce protective immunity against *S. aureus* in a patient. The composition comprises a pharmaceutically acceptable carrier and an immunologically effective amount of an immunogen providing protective immunity against *S. aureus*.

An immunologically effective amount is an amount sufficient to provide protective immunity against *S. aureus* infection. The amount should be sufficient to significantly prevent the likelihood or severity of a S. aureus infection.

Another aspect of the present invention describes a nucleic acid comprising a recombinant gene encoding a polypeptide that provides protective immunity against S. aureus. A recombinant gene contains recombinant nucleic acid encoding a polypeptide along with regulatory elements for proper transcription and processing (which may include translational and post translational elements). The recombinant gene can exist independent of a host genome or can be part of a host genome.

A recombinant nucleic acid is nucleic acid that by virtue of its sequence and/or form does not occur in nature. Examples of recombinant nucleic acid include purified nucleic acid, two or more nucleic acid regions combined together that provide a different nucleic acid than found in nature, and the absence of one or more nucleic acid regions (e.g., upstream or downstream regions) that are naturally associated with each other.

Another aspect of the present invention describes a recombinant cell. The cell comprises a recombinant gene encoding a polypeptide that provides protective immunity against S. aureus.

Another aspect of the present invention describes a method of making a polypeptide that provides protective immunity against S. aureus. The method involves growing a recombinant cell containing recombinant nucleic acid encoding the polypeptide and purifying the polypeptide.

Another aspect of the present invention describes a polypeptide that provides protective immunity against S. aureus made by a process comprising the steps of growing a recombinant cell containing recombinant nucleic acid encoding the polypeptide in a host and purifying the polypeptide. Different host cells can be employed.

Another aspect of the present invention describes an isolated AhpC-AhpF binding protein. The binding protein comprises an antibody variable region that binds to an AhpC-AhpF complex.

Reference to "isolated" indicates a different form than found in nature. The different form can be, for example, a different purity than found in nature and/or a structure that is not found in nature. A structure not found in nature includes recombinant structures where different regions are combined together, for example, humanized antibodies where one or more murine complementary determining regions (CDR) is inserted onto a human framework scaffold, hybrid antibodies where one or more CDR from an antibody binding protein is inserted into a different framework scaffold, and antibodies derived from natural human sequences where genes coding light and heavy variable domains were randomly combined together.

The isolated protein is preferably substantially free of serum proteins. A protein substantially free of serum proteins is present in an environment lacking most or all serum proteins.

Another aspect of the present invention describes a method of treating a patient against S. aureus infection. The method comprises the step of administering to the patient one or more of the following:

(a) an immunologically effective amount of an immunogen comprising an amino acid sequence at least 85% identical to SEQ ID NO: 1 or a fragment of SEQ ID NO: 1, wherein the polypeptide provides protective immunity against S. aureus;

(b) an immunogenic composition comprising a polypeptide at least 85% identical to SEQ ID NO: 1 and a polypeptide at least 85% identical to SEQ ID NO: 3; or (c) an effective amount of an AhpC-AhpF binding protein.

Unless particular terms are mutually exclusive, reference to "or" indicates either or both possibilities. Occasionally phrases such as "and/or" are used to highlight either or both possibilities.

Reference to open-ended terms such as "comprises" allows for additional elements or steps. Occasionally phrases such as "one or more" are used with or without open-ended terms to highlight the possibility of additional elements or steps.

Unless explicitly stated reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 illustrates the amino acid sequence of SEQ ID NO: 1 and SEQ ID NO: 2. The entire sequence is SEQ ID NO: 2. The portion shown in bold is SEQ ID NO: 1. The underlined regions are an amino His-tag region and additional amino acids at the carboxyl end.

FIG. 2 illustrates a sequence comparison between AhpC sequences frog S. aureus (SEQ ID NO: 1) and S. epidermidis (SEQ ID NO: 6, GenBank Accession No. AE016752). Amino acid differences are shown in bold.

FIG. 3 illustrates a nucleic acid sequence (SEQ ID NO: 5) encoding SEQ ID NO: 2. The additional His-tag and carboxyl amino acids encoding region are shown in bold.

FIG. 4 illustrates a DNA sequence (SEQ ID NO: 4) encoding for SEQ ID NO: 3.

FIGS. 5A and 5B illustrate a sequence comparison between different AhpF sequences from S. aureus: SEQ ID NOs: 3 (GenBank Accession No. U92441), 9 (GenBank Accession No. AP004823), and 10 (GenBank Accession No. BX57183) and S. epidermidis, SEQ ID NO: 8 (GenBank Accession No. AE016752). Amino acid differences are shown in bald.

DETAILED DESCRIPTION OF THE INVENTION

Figure 6A:
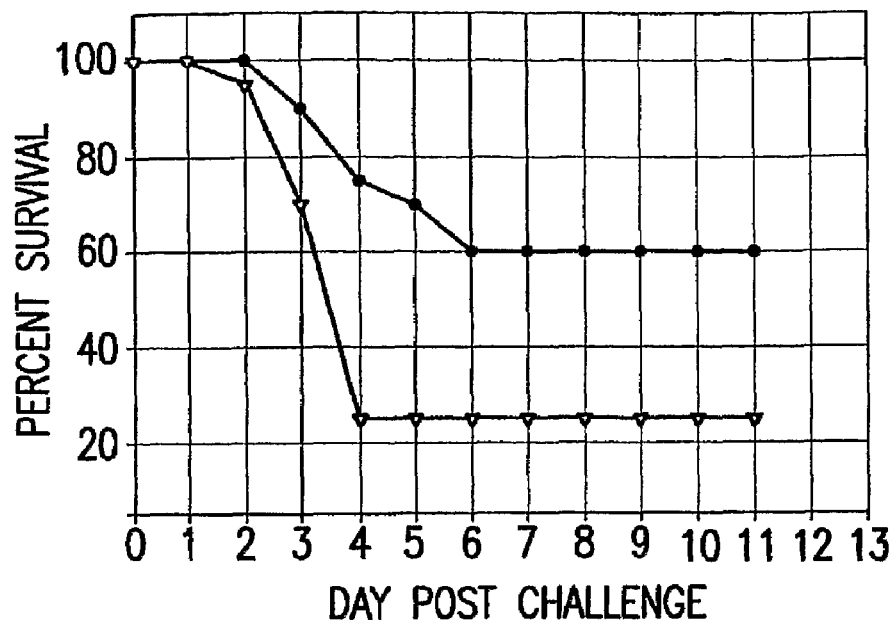
FIGS. 6A and 6B illustrate results from experiments using either a SEQ ID NO: 2 polypeptide (closed circles) in aluminum hydroxyphosphate adjuvant, or the adjuvant alone (triangles).

The ability of SEQ ID NO: 1 related polypeptides to provide protective immunity is illustrated in the Examples provided below using SEQ ID NO: 2. SEQ ID NO: 2 is a derivative of SEQ ID NO: 1 containing an amino His-tag and three additional carboxyl amino acids. The His-tag facilitates polypeptide purification and identification.

Polypeptides structurally related to SEQ ID NO: 1 include polypeptides containing corresponding regions present in different S. aureus strains and derivatives of naturally occurring regions. The amino acid sequence of SEQ ID NO: 1 is illustrated by the bold region in FIG. 1. FIG. 1 also illustrates the amino His-tag present and additional carboxyl amino acids present in SEQ ID NO: 2.

I. AhpC Sequences

S. aureus AhpC was initially identified as a protein induced by osmotic up shock having extensive similarity to E. coli alkyl hydroperoxide reductase (AhpC). (Amstrong-Buisseret et al., *Microbiology* 141:1655-1661, 1995.) AhpC homologs of varying similarity are present in mammalian brain and in different organisms, including numerous bacterial species. (Chae et al., *Proc. Natl. Acad. Sci. USA* 91:7017-7021, 1994, Yan et al., *Helicobacter* 6:274-282, 2001.)

S. aureus AhpC related sequences have been given different designations in different references. Examples of different designations are provided in TIGR (SA0452); Baba et al., *Lancet* 359:1819-1827, 2002 (MW0357); Kuroda et al., *Lancet* 357:1225-1240, 2001 (SAV0381); and Ohta et al., *DNA Research* 1:51, 2004 (SAV0381 and SAV0773).

FIG. 2 provides a sequence comparison for S. aureus AhpC related sequences present in S. aureus (SEQ ID NO: 1) and S. epidermidis (SEQ ID NO: 6). Additional comparisons can be performed from other AhpC sequences.

Other naturally occurring AhpC sequences can be identified based on the presence of a high degree of sequence similarity or contiguous amino acids compared to a known AhpC sequence. Contiguous amino acids provide characteristic tags. In different embodiments, a naturally occurring AhpC sequence is a sequence found in a *Staphylococcus*, preferably S. aureus, having at least 20, at least 30, or at least 50 contiguous amino acids as in SEQ ID NO: 1; and/or having at least 85% sequence similarity or identity with SEQ ID NO: 1.

Sequence similarity can be determined by different algorithms and techniques well known in the art. Generally, sequence similarity is determined by techniques aligning two sequences to obtain maximum amino acid identity, allowing for gaps, additions and substitutions in one of the sequences.

Sequence similarity can be determined, for example, using a local alignment tool utilizing the program lalign (developed by Huang and Miller, *Adv. Appl. Math.* 12:337-357, 1991, for the <<sim>> program). The options and environment variables are: −f # Penalty for the first residue a gap (−14 by default); −g # Penalty for each additional residue in a gap (−4 by default)-s str (SMATRIX) the filename of an alternative scoring matrix file. For protein sequences, PAM250 is used by default-w # (LINLEN) output line length for sequence alignments (60).

II. SEQ ID NO: 1 Related Polypeptides

SEQ ID NO: 1 related polypeptides contain an amino acid sequence at least 85% identical to SEQ ID NO: 1. Reference to "polypeptide" does not provide a minimum or maximum size limitation.

A polypeptide at least 85% identical to SEQ ID NO: 1 contains up to about 28 amino acid alterations from SEQ ID NO: 1. Each amino acid alteration is independently either an amino acid substitution, deletion, or addition. In different embodiments, the SEQ ID NO: 1 related polypeptide is at least 90%, at least 94%, or at least 99% identical to SEQ ID NO: 1; differs from SEQ ID NO: 1 by 0, 1, 2, 3, 4, 5, 6, 7, 8, 9, 10, 11, 12, 13, 14, 15, 16, 17, 18, 19, or 20 amino acid alterations; or consists essentially of SEQ ID NO: 1.

An embodiment of the present invention features a polypeptide immunogen comprising or consisting essentially of a sequence at least 85%, at least 95%, or 100% identical to amino acids 178-189 of SEQ ID NO: 1. In further embodiments, the polypeptide comprising amino acids 178-189 of SEQ ID NO: 1 consists of no more than 13, 15, 20, 25, 50, 100, or 150 amino acids in total; and/or the overall polypeptide is at least 85%, at least 90%, or identical to a SEQ ID NO: 1 region and comprises amino acids 178-189 of SEQ ID NO: 1. Additional amino acids that may be present include additional SEQ ID NO: 1 amino acids or other amino acid regions. A preferred additional amino acid is an amino terminus methionine.

Reference to "consists essentially" of indicated amino acids indicates that the referred to amino acids are present and additional amino acids may be present. The additional amino acids can be at the carboxyl or amino terminus. In different embodiments 1, 2, 3, 4, 5, 6, 7, 8, 9, 10, 11, 12, 13, 14, 15, 16, 17, 18, 19, or 20 additional amino acids are present.

Alterations can be made to SEQ ID NO: 1 polypeptides and fragments thereof to obtain derivatives that induce protective immunity against S. aureus. Alterations can be performed, for example, to obtain a derivative retaining the ability to induce protective immunity against S. aureus or to obtain a derivative that in addition to providing protective immunity also has a region that can achieve a particular purpose.

The sequence comparison provided in FIG. 2, and a comparison with other S. aureus AhpC sequences, can be used to guide the design of potential alterations. In addition, alterations can be made taking into account known properties of amino acids.

Generally, in substituting different amino acids to retain activity it is preferable to exchange amino acids having similar properties. Factors that can be taken into account for an amino acid substitution include amino acid size, charge, polarity, and hydrophobicity. The effect of different amino acid R-groups on amino acid properties are well known in the art. (See, for example, Ausubel, *Current Protocols in Molecular Biology*, John Wiley, 1987-2002, Appendix 1C.)

In exchanging amino acids to maintain activity, the replacement amino acid should have one or more similar properties such as approximately the same charge and/or size and/or polarity and/or hydrophobicity. For example, substituting valine for leucine, arginine fox lysine, and asparagine for glutamine are good candidates for not causing a change in polypeptide functioning.

Alterations to achieve a particular purpose include those designed to facilitate production or efficacy of the polypeptide; or cloning of the encoded nucleic acid. Polypeptide production can be facilitated through the use of an initiation codon (e.g., coding for methionine) suitable for recombinant expression. The methionine may be later removed during cellular processing. Cloning can be facilitated by, for example, the introduction of restriction sites which can be accompanied by amino acid additions or changes.

Efficacy of a polypeptide to induce an immune response can be enhanced through epitope enhancement. Epitope enhancement can be performed using different techniques such as those involving alteration of anchor residues to improve peptide affinity for MHC molecules and those increasing affinity of the peptide-MHC complex for a T-cell receptor. (Berzofsky et al., *Nature Review* 1:209-219, 2001.)

Preferably, the polypeptide is a purified polypeptide. A "purified polypeptide" is present in an environment lacking one or more other polypeptides with which it is naturally associated and/or is represented by at least about 10% of the total protein present. In different embodiments, the purified polypeptide represents at least about 50%, at least about 75%, or at least about 95% of the total protein in a sample or preparation.

In an embodiment, the polypeptide is "substantially purified." A substantially purified polypeptide is present in an environment lacking all, or most, other polypeptides with which the polypeptide is naturally associated. For example, a substantially purified S. aureus polypeptide is present in an environment lacking all, or most, other *S. aureus* polypeptides. An environment can be, for example, a sample or preparation.

Reference to "purified" or "substantially purified" does not require a polypeptide to undergo any purification and may include, for example, a chemically synthesized polypeptide that has not been purified.

Polypeptide stability can be enhanced by modifying the polypeptide carboxyl or amino terminus. Examples of possible modifications include amino terminus protecting groups such as acetyl, propyl, succinyl, benzyl, benzyloxycarbonyl or t-butyloxycarbonyl; and carboxyl terminus protecting groups such as amide, methylamide, and ethylamide.

In an embodiment of the present invention the polypeptide immunogen is part of an immunogen containing one or more additional regions or moieties covalently joined to the polypeptide at the carboxyl terminus or amino terminus, where each region or moiety is independently selected from a region or moiety having at least one of the following properties: enhances the immune response, facilitates purification, or facilitates polypeptide stability. Polypeptide stability can be enhanced, for example, using groups such as polyethylene glycol that may be present on the amino or carboxyl terminus.

Polypeptide purification can be enhanced by adding a group to the carboxyl or amino terminus to facilitate purification. Examples of groups that can be used to facilitate purification include polypeptides providing affinity tags. Examples of affinity tags include a six-histidine tag, trpE, glutathione and maltose-binding protein.

The ability of a polypeptide to produce an immune response can be enhanced using groups that generally enhance an immune response. Examples of groups that can be joined to a polypeptide to enhance an immune response against the polypeptide include cytokines such as IL-2. (Buchan et al., 2000. *Molecular Immunology* 37:545-552.)

III. AhpC-AhpF Immunogens

An AhpC-AhpF immunogen is a composition containing an AhpC and an AhpF component. The AhpC component is made up of a SEQ ID NO: 1 related polypeptide. The AhpF component is made up of a SEQ ID NO: 3 related polypeptide.

SEQ ID NO: 1 related polypeptides contain an amino acid sequence at least 85% identical to SEQ ID NO: 1. Different embodiments of SEQ ID NO: 1 related polypeptides are described in Section II supra.

SEQ ID NO: 3 related polypeptides contain an amino acid sequence at least 85% identical to SEQ ID NO: 3. Each amino acid alteration is independently either an amino acid substitution, deletion, or addition. In different embodiments, the SEQ ID NO: 3 related polypeptide is at least 90%, at least 94%, at least 99%, or identical to SEQ ID NO: 3; differs from SEQ ID NO: 3 by 0, 1, 2, 3, 4, 5, 6, 7, 8, 9, 10, 11, 12, 13, 14, 15, 16, 17, 18, 19, or 20 amino acid alterations; or consists essentially of SEQ ID NO: 3.

Alterations can be made to SEQ ID NO: 3 related polypeptides to obtain derivatives used with the SEQ ID NO: 1 related polypeptide component. Alterations can be performed, for example, to obtain an overall composition retaining the ability to induce protective immunity against *S. aureus* or to obtain an overall composition that in addition to providing protective immunity also has a region that can achieve a particular purpose.

Examples of different AhpF sequences that can be used to aid in the design of the AhpF component are provided in FIGS. 5A and 5B. Additional guidance for producing alterations to a polypeptide are provided in Section II supra.

*S. aureus* AhpF related sequences have been given different designations in different references. Examples of different designations are provided in TIGR (SA0451); Baba et al., *Lancet* 359:1819-1827, 2002 (MWO356); Kuroda et al., *Lancet* 357:1225-1240, 2001 (SAV0380 and SA0365); and Enright et al., *PNAS* 99:9786-9791, 2002 (SAS0357 and SAR0398).

AhpC and AhpF composition are preferably produced recombinantly using constructs expressing both components. For example, an *E. coli* strain can be engineered to coexpress ahpC and ahpF and the AhpC and AhpF complex can be isolated. Additional guidance and examples for polypeptide production is provided in Section IV infra.

IV. Polypeptide Production

Polypeptides can be produced using standard techniques including those involving chemical synthesis and those involving purification from a cell producing the polypeptide. Techniques for chemical synthesis of polypeptides are well known in the art. (See e.g., Vincent, *Peptide and Protein Drug Delivery*, New York, N.Y., Decker, 1990.) Techniques for recombinant polypeptide production and purification are also well known in the art. (See for example, Ausubel, *Current Protocols in Molecular Biology*, John Wiley, 1987-2002.)

Obtaining polypeptides from a cell is facilitated using recombinant nucleic acid techniques to produce the polypeptide. Recombinant nucleic acid techniques for producing a polypeptide involve introducing, or producing, a recombinant gene encoding the polypeptide in a cell and expressing the polypeptide.

A recombinant gene contains nucleic acid encoding a polypeptide along with regulatory elements for polypeptide expression. The recombinant gene can be present in a cellular genome or can be part of an expression vector.

The regulatory elements that may be present as part of a recombinant gene include those naturally associated with the polypeptide encoding sequence and exogenous regulatory elements not naturally associated with the polypeptide encoding sequence. Exogenous regulatory elements such as an exogenous promoter can be useful for expressing a recombinant gene in a particular host or increasing the level of expression. Generally, the regulatory elements that are present in a recombinant gene include a transcriptional promoter, a ribosome binding site, a terminator, and an optionally present operator. A preferred element for processing in eukaryotic cells is a polyadenylation signal.

Expression of a recombinant gene in a cell is facilitated through the use of an expression vector. Preferably, an expression vector in addition to a recombinant gene also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Due to the degeneracy of the genetic code, a large number of different encoding nucleic acid sequences can be used to code for a particular polypeptide. The degeneracy of the genetic code arises because almost all amino acids are encoded by different combinations of nucleotide triplets or "codons". Amino acids are encoded by codons as follows:

A = Ala = Alanine:        codons GCA, GCC, GCG, GCU

C = Cys = Cysteine:       codons UGC, UGU

D = Asp = Aspartic acid:  codons GAC, GAU

-continued

```
E = Glu = Glutamic acid:  codons GAA, GAG
F = Phe = Phenylalanine:  codons UUC, UUU
G = Gly = Glycine:        codons GGA, GGC, GGG, GGU
H = His = Histidine:      codons CAC, CAU
I = Ile = Isoleucine:     codons AUA, AUC, AUU
K = Lys = Lysine:         codons AAA, AAG
L = Leu = Leucine:        codons UUA, UUG, CUA, CUC,
                          CUG, CUU
M = Met = Methionine:     codon AUG
N = Asn = Asparagine:     codons AAC, AAU
P = Pro = Proline:        codons CCA, CCC, CCG, CCU
Q = Gln = Glutamine:      codons CAA, CAG
R = Arg = Arginine:       codons AGA, AGG, CGA, CGC,
                          CGG, CGU
S = Ser = Serine:         codons AGC, AGU, UCA, UCC,
                          UCG, UCU
T = Thr = Threonine:      codons ACA, ACC, ACG, ACU
V = Val = Valine:         codons GUA, GUC, GUG, GUU
W = Trp = Tryptophan:     codon UGG
Y = Tyr = Tyrosine:       codons UAC, UAU
```

Suitable cells for recombinant nucleic acid expression of SEQ ID NO: 1 or SEQ ID NO: 3 related polypeptides are prokaryotes and eukaryotes. Examples of prokaryotic cells include *E. coli*; members of the *Staphylococcus* genus, such as *S. aureus*; members of the *Lactobacillus* genus, such as *L. plantarum*; members of the *Lactococcus* genus, such as *L. lactis*; and members of the *Bacillus* genus, such as *B. subtilis*. Examples of eukaryotic cells include mammalian cells; insect cells; yeast cells such as members of the *Saccharomyces* genus (e.g., *S. cerevisiae*), members of the *Pichia* genus (e.g., *P. pastoris*), members of the *Hansenula* genus (e.g., *H. polymorpha*), members of the *Kluyveromyces* genus (e.g., *K. lactis* or *K. fragilis*) and members of the *Schizosaccharomyces* genus (e.g., *S. pombe*).

Techniques for recombinant gene production, introduction into a cell, and recombinant gene expression are well known in the art. Examples of such techniques are provided in references such as Ausubel, *Current Protocols in Molecular Biology*, John Wiley, 1987-2002, and Sambrook et al., *Molecular Cloning, A Laboratory Manual*, 2nd Edition, Cold Spring Harbor Laboratory Press, 1989.

If desired, expression in a particular host can be enhanced through codon optimization. Codon optimization includes use of more preferred codons. Techniques for codon optimization in different hosts are well known in the art.

Polypeptides may contain post translational modifications, for example, N-linked glycosylation, O-linked glycosylation, or acetylation. Reference to "polypeptide" or an "amino acid" sequence of a polypeptide includes polypeptides containing one or more amino acids having a structure of a post-translational modification from a host cell, such as a yeast host.

Post translational modifications can be produced chemically or by making use of suitable hosts. For example, in *S. cerevisiae* the nature of the penultimate amino acid appears to determine whether the N-terminal methionine is removed. Furthermore, the nature of the penultimate amino acid also determines whether the N-terminal amino acid is N'-acetylated (Huang et al., *Biochemistry* 26: 8242-8246, 1987). Another example includes a polypeptide targeted for secretion due to the presence of a secretory leader (e.g., signal peptide), where the protein is modified by N-linked or O-linked glycosylation. (Kukuruzinska et al., *Ann. Rev. Biochem.* 56:915-944, 1987.)

V. Adjuvants

Adjuvants are substances that can assist an immunogen in producing an immune response. Adjuvants can function by different mechanisms such as one or more of the following: increasing the antigen biologic or immunologic half-life; improving antigen delivery to antigen-presenting cells; improving antigen processing and presentation by antigen-presenting cells; and inducing production of immunomodulatory cytokines. (Vogel, *Clinical Infectious Diseases* 30 (suppl. 3):S266-270, 2000.)

A variety of different types of adjuvants can be employed to assist in the production of an immune response. Examples of particular adjuvants include aluminum hydroxide, aluminum phosphate, or other salts of aluminum, calcium phosphate, DNA CpG motifs, monophosphoryl lipid A, cholera toxin, *E. coli* heat-labile toxin, pertussis toxin, muramyl dipeptide, Freund's incomplete adjuvant, MF59, SAF, immunostimulatory complexes, liposomes, biodegradable microspheres, saponins, nonionic block copolymers, muramyl peptide analogues, polyphosphazene, synthetic polynucleotides, IFN-γ, IL-2, IL-12, and ISCOMS. (Vogel *Clinical Infectious Diseases* 30 (suppl 3):S266-270, 2000, Klein et al., *Journal of Pharmaceutical Sciences* 89:311-321, 2000, Rimmelzwaan et al., *Vaccine* 19:1180-1187, 2001, Kersten *Vaccine* 21:915-920, 2003, O'Hagen *Curr. Drug Target Infect. Disord.*, 1:273-286, 2001.)

VI. Patients

A "patient" refers to a mammal capable of being infected with *S. aureus*. A patient can be treated prophylactically or therapeutically. Prophylactic treatment provides sufficient protective immunity to reduce the likelihood, or severity, of a *S. aureus* infection. Therapeutic treatment can be performed to reduce the severity of a *S. aureus* infection.

Prophylactic treatment can be performed using a vaccine containing an immunogen described herein. Such treatment is preferably performed on a human. Vaccines can be administered to the general population or to those persons at an increased risk of *S. aureus* infection.

Persons with an increased risk of *S. aureus* infection include health care workers; hospital patients; patients with a weakened immune system; patients undergoing surgery; patients receiving foreign body implants, such as a catheter or a vascular device; patients facing therapy leading to a weakened immunity; and persons in professions having an increased risk of burn or wound injury. (*The Staphylococci in Human Disease*, Crossley and Archer (ed.), Churchill Livingstone Inc. 1997.)

Non-human patients that can be infected with *S. aureus* include cows, pigs, sheep, goats, rabbits, horses, dogs, cats, monkeys, rats, and mice. Treatment of non-human patients is useful in protecting pets and livestock, and in evaluating the efficacy of a particular treatment.

VII. Combination Vaccines

Immunogens described herein can be used alone, or in combination with other immunogens, to induce an immune response. Additional immunogens that may be present include: one or more additional *S. aureus* immunogens, such as those referenced in the Background of the Invention supra; one or more immunogens targeting one or more other *Staphylococcus* organisms such as *S. epidermidis, S. haemolyticus, S. warneri*, or *S. lugunensis*; and one or more immunogens targeting other infections organisms.

VIII. Animal Model System

An animal model system was used to evaluate the efficacy of an immunogen to produce a protective immune response against *S. aureus*. The animal model was a slow kinetics lethality model involving *S. aureus* prepared from cells in stationary phase, appropriately titrated, and intravenously administered. This slow kinetics of death provides sufficient time for the specific immune defense to fight off the bacterial infection (e.g., 10 days rather 24 hours).

*S. aureus* cells in stationary phase can be obtained from cells grown on solid medium. They can also be obtained from liquid, however the results with cells grown on solid medium were more reproducible. Cells can conveniently be grown overnight on solid medium. For example, *S. aureus* can be grown from about 18 to about 24 hours under conditions where the doubling time is about 20-30 minutes.

*S. aureus* can be isolated from solid or liquid medium using standard techniques to maintain *S. aureus* potency. Isolated *S. aureus* can be stored, for example, at $-70°$ C. as a washed high density suspension ($>10^9$ colony forming units (CFU)/mL) in phosphate buffered saline containing glycerol.

The *S. aureus* challenge should have a potency providing about 80 to 90% death in an animal model over a period of about 7 to 10 days starting on the first or second day. Titration experiments can be performed using animal models to monitor the potency of the stored *S. aureus* inoculum. The titration experiments can be performed about one to two weeks prior to an inoculation experiment.

IX. Antibodies

Immunogens containing SEQ ID NO: 1 related polypeptides and AhpC-AhpF compositions can be used to produce isolated binding proteins that bind to the immunogen or to *S. aureus*. Such binding proteins have different uses including use in polypeptide purification, *S. aureus* identification, or in therapeutic or prophylactic treatment against *S. aureus* infection. Preferably, the binding protein is substantially free of serum proteins.

A binding protein comprises a first variable region and a second variable region. The variable regions have the structure of an antibody variable region from a heavy or light chain. Antibody heavy and light chain variable regions contain three complementary determining regions interspaced onto a framework. The complementary determining regions are primarily responsible for recognizing a particular epitope. Examples of antibody binding protein include single-chain antibodies, a complete antibody, an antibody fragment, and derivatives thereof.

A preferred antigen binding protein is a monoclonal antibody. Reference to a "monoclonal antibody" indicates a collection of antibodies having the same, or substantially the same, complementary determining region and binding specificity. The variation in the monoclonal antibodies is that which would occur if the antibodies were produced from the same construct(s).

Monoclonal antibodies can be produced, for example, from a particular hybridoma and from a recombinant cell containing one or more recombinant genes encoding the antibody. The antibody may be encoded by more than one recombinant gene where, for example, one gene encodes the heavy chain and one gene encodes the light chain.

Antibody fragments containing an antibody variable region include Fv, Fab, and $Fab_2$ regions. Each Fab region contains a light chain made up of a variable region and a constant region, and a heavy chain region containing a variable region and a constant region. A light chain is joined to a heavy chain by disulfide bonding through constant regions. The light and heavy chain variable regions of a Fab region provide for an Fv region that participates in antigen binding.

The antibody variable region can also be part of protein containing variable regions such as single chain antibody and a minibody. A single chain antibody contains a light and a heavy variable region joined together by a linker. The linker can be, for example, about 5 to 16 amino acids. A minibody is a single chain-CH3 fusion protein that self assembles into a bivalent dimer of about 80 kDa.

Specificity of the variable region is determined by three hypervariable regions (also referred to as complementarity determining regions), that are interposed between more conserved flanking regions (also referred to as framework regions). Amino acids associated with framework regions and complementarity determining regions can be numbered and aligned as described by Kabat et al., Sequences of Proteins of Immunological Interest, U.S. Department of Health and Human Services, 1991.

Techniques for generating antigen binding protein such as a single-chain antibody, an antibody, or an antibody fragment are well known in the art. Examples of such techniques include the use of phage display technology, identification and humanization of rodent antibodies, and generation of human antibodies using a XenoMouse or Trans-Chromo mouse. (E.g., Azzazy et al., *Clinical Biochemistry* 35:425-445, 2002, Berger et al., *Am. J. Med. Sci.* 324(1):14-40, 2002.)

Murine antibodies can be humanized, and CDR's, can be grafted on to human antibody frameworks using techniques well known in art. Such techniques are generally described with reference to humanizing murine antibodies by grafting murine variable regions onto a human antibody framework and, if needed making further modifications. (E.g., O'Brien et al., Humanization of Monoclonal Antibodies by CDR Grafting, p 81-100, From *Methods in Molecular Biology* Vol 207: *Recombinant antibodies for Cancer Therapy: Methods and Protocols* (Eds. Welschof and Krauss) Humana Press, Totowa, N.J., 2003.)

Antigen binding protein are preferably produced using recombinant nucleic acid techniques or through the use of a hybridoma. Recombinant nucleic acid techniques involve constructing a nucleic acid template for protein synthesis. A hybridoma is an immortalized cell line producing the antigen binding protein.

Recombinant nucleic acid encoding an antigen binding protein can be expressed in a host cell that in effect serves as a factory for the encoded protein. The recombinant nucleic acid can provide a recombinant gene encoding the antigen binding protein that exists autonomously from a host cell genome or as part of the host cell genome.

A recombinant gene contains nucleic acid encoding a protein along with regulatory elements for protein expression. Generally, the regulatory elements that are present in a recombinant gene include a transcriptional promoter, a ribosome binding site, a terminator, and an optionally present operator. A preferred element for processing in eukaryotic cells is a polyadenylation signal. Antibody associated introns may also be present. Examples of expression cassettes for antibody or antibody fragment production are well known in art. (E.g., Persic et al., *Gene* 187:9-18, 1997, Boel et al., *J.*

Immunol. Methods 239:153-166, 2000, Liang et al., J. Immunol. Methods 247:119-130, 2001.)

Expression of a recombinant gene in a cell is facilitated using an expression vector. Preferably, an expression vector, in addition to a recombinant gene, also contains an origin of replication for autonomous replication in a host cell, a selectable marker, a limited number of useful restriction enzyme sites, and a potential for high copy number. Examples of expression vectors for antibody and antibody fragment production are well known in art. (E.g., Persic et al., Gene 187: 9-18, 1997, Boel et al., J. Immunol. Methods 239:153-166, 2000, Liang et al., J. Immunol. Methods 247:119-130, 2001.)

If desired, nucleic acid encoding an antibody may be integrated into the host chromosome using techniques well known in the art. (See, Ausubel, Current Protocols in Molecular Biology, John Wiley, 1987-1998, Mark et al., U.S. Pat. No. 6,743,622.)

A variety of different cell lines can be used for recombinant antigen binding protein expression, including those from prokaryotic organisms (e.g., E. coli, Bacilli, and Streptomyces) and from Eukaryotic (e.g., yeast, Baculovirus, and mammalian). (Breitling et al., Recombinant Antibodies, John Wiley & Sons, Inc. and Spektrum Akademischer Verlag, 1999.)

Preferred hosts for recombinant antigen binding protein expression are mammalian cells able to produce antigen binding protein with proper post translational modifications. Post translational modifications include disulfide bond formation and glycosylation. Another type of post translational modification is signal peptide cleavage.

Proper glycosylation can be important for antibody function. (Yoo et al., Journal of Immunological Methods 261:1-20, 2002.) Naturally occurring antibodies contain at least one N-linked carbohydrate attached to a heavy chain. (Id.) Additional N-linked carbohydrates and O-linked carbohydrates may be present and may be important for antibody function. (Id.)

Different types of mammalian host cells can be used to provide for efficient post-translational modifications. Examples of such host cells include Chinese hamster ovary (CHO), HeLa, C6, PC12, and myeloma cells. (Yoo et al., Journal of Immunological Methods 261:1-20, 2002, Persic et al., Gene 187:9-18, 1997.)

A hybridoma can be produced using techniques such as those described in Ausubel Current Protocols in Molecular Biology, John Wiley, 1987-1998, Harlow et al, Antibodies, A Laboratory Manual, Cold Spring Harbor Laboratory, 1988, and Kohler et al., Nature 256, 495-497, 1975.

X. Administration

Immunogens and binding protein can be formulated and administered to a patient using the guidance provided herein along with techniques well known in the art. Guidelines for pharmaceutical administration in general are provided in, for example, Vaccines Eds. Plotkin and Orenstein, W.B. Sanders Company, 1999; Remington's Pharmaceutical Sciences 20$^{th}$ Edition, Ed. Gennaro, Mack Publishing, 2000; and Modern Pharmaceutics 2$^{nd}$ Edition, Eds. Banker and Rhodes, Marcel Dekker, Inc., 1990, each of which are hereby incorporated by reference herein.

Pharmaceutically acceptable carriers facilitate storage and administration of an immunogen to a patient. Pharmaceutically acceptable carriers may contain different components such as a buffer, sterile water for injection, normal saline or phosphate buffered saline, sucrose, histidine, salts and polysorbate.

Immunogens and binding protein can be administered by different routes such as subcutaneous, intramuscular, or mucosal. Subcutaneous and intramuscular administration can be performed using, for example, needles or jet-injectors.

Suitable dosing regimens are preferably determined taking into account factors well known in the art including age, weight, sex and medical condition of the patient; the route of administration; the desired effect; and the particular compound employed. The immunogen or binding protein can be used in multi-dose formats. It is expected that a dose would consist of the range of 1.0 μg to 1.0 mg total polypeptide, in different embodiments of the present invention the range is 0.01 mg to 1.0 mg and 0.1 mg to 1.0 mg.

The timing of doses depends upon factors well known in the art. After the initial administration one or more booster doses may subsequently be administered to maintain or boost antibody titers. An example of a dosing regime would be day 1, 1 month, a third dose at either 4, 6 or 12 months, and additional booster doses at distant times as needed.

EXAMPLES

Examples are provided below further illustrating different features of the present invention. The examples also illustrate useful methodology for practicing the invention. These examples do not limit the claimed invention.

Example 1

Protective Immunity

This example illustrates the ability of SEQ ID NO: 1 related polypeptides to provide protective immunity in an animal model. SEQ ID NO: 2, a His-tagged derivative of SEQ ID NO: 1, was used to provide protective immunity.

SEQ ID NO: 2 Cloning and Expression

The protein encoded by COL SA0452 was designed to be expressed from the pET16b vector (EMD Biosciences, Madison, Wis.) with the N-terminal histidine residues and the stop codon encoded by the vector. Also encoded by the vector are nine additional amino acids after the histidine tag and three additional amino acids at the carboxyl terminus. PCR primers were designed to amplify COL SA0452 starting at the first serine codon and ending prior to the stop codon at the terminal isoleucine residue. The forward and reverse primers were: 5'GGGAATTCCATATGTCATTAATTAA-CAAAGAAATCTTACC3' (SEQ ID NO: 7) and 5'GGGCT-CAGCGATTTTACCTACTAAATCTAAACCAG3' (SEQ ID NO: 11), respectively and contained additional restriction sites (underlined), i.e., NdeI (forward primer) and Bpu1102I (reverse primer) and a GC clamp to facilitate cloning into the expression vector.

Genomic DNA was purified from S. aureus COL strain MB5393 and used as template for PCR. A 50-mL culture was grown overnight in DIFCO Tryptic Soy Broth (Becton Dickinson, Sparks, Md.) at 37° C. and the cells were collected by centrifugation. The cells were washed once in 5 mL of 10 mM Tris pH 7.5, 25% sucrose and resuspended in the same solution containing 50 μg/mL lysostaphin (Sigma, St. Louis, Mo.). The mixture was incubated at 37° C. for 1 hour and subsequently, 2.5 mL of 0.25 M EDTA pH 8.0 was added. After incubation for 15 minutes on ice, 7.5 mL 2% sarkosyl was added and the mixture was swirled gently and allowed to sit for 30 more minutes on ice. One-hundred fifty μL RNAse, 5 mg/mL in 0.1 M sodium acetate, was added and the mixture was incubated for one hour at 37° C. Next, 0.6 mL proteinase K, 25 mg/mL, was added and the incubation was continued for 2 hours followed by an overnight incubation at 4° C. The lysate was extracted with 15 mL water-saturated phenol by gentle rotation for 30 minutes at room temperature.

To separate phases the mixture was centrifuged at 4,000 rpm for 10 minutes at room temperature. The aqueous phase was collected and the phenol extraction was repeated two more times. Next, the aqueous phase was extracted ten times with an equal volume of chloroform. After the last extraction, the aqueous phase was collected, the volume was measured, and one half volume 7.5 M ammonium acetate was added.

The DNA was precipitated by adding two volumes of 100% ethanol and collected by spooling with a glass rod. The DNA was dissolved in 5.0 mL TE containing 4 µL diethylpyrocarbonate overnight at 4° C. The ethanol precipitations were repeated two more times.

The ahpC gene was amplified by PCR in a 50 µL volume reaction prepared in duplicate. Each contained 250 ng genomic DNA, 125 ng each forward and reverse primer, 1 microliter 10 mM dNTPs, 2.5 units of native Pfu polymerase and 1X Pfu buffer (Stratagene, La Jolla Calif.). The thermacycling conditions were as follows: one cycle of 94° C. for 5 minutes; 30 cycles of 94° C. for 45 seconds, 56° C. for 45 seconds, 72° C. for one minute; one cycle of 72° C. for 10 minutes. The amplified DNA sequence (584 bp) was digested with the appropriate restriction enzymes and gel-purified using GENE CLEAN II®(QBIOgene, Carlsbad, Calif.) according to the manufacturer's directions. The DNA was ligated into the pET16b vector using the NdeI/Bpu1102I sites that had been engineered into the PCR primers and introduced into E. coli NovaBlue competent cells (EMD Biosciences).

The transformation mixture was grown overnight at 37° C. on low salt Lennox L Broth agar plates containing 100 µg/mL each ampicillin, IPTG, and X-gal, prepared using IMMEDIA™ Amp Agar (Invitrogen, Carlsbad, Calif.), according to the manufacturer's instructions. Colonies were selected and grown in Luria Broth (LB) with 50 µg/mL ampicillin, DNA minipreps were made (Promega), and the appropriate insert was determined by restriction endonuclease digestion. The plasmid DNA from two minipreps was sequenced, and a clone containing no DNA changes from the desired sequence was selected and designated pAhpC5.

E. coli BLR (DE3) competent cells (EMD Biosciences) were transformed with pAhpC5 and grown on LB plates containing ampicillin (100 µg/mL). To test for expression of ahpC, an isolated colony was inoculated into 5 mL of liquid LB (ampicillin) and incubated at 37° C., 220 rpm for 6 hours. The culture was held overnight at 4° C. and inoculated the next day into 20.0 mL LB broth (ampicillin) such that the starting $OD_{600}$ equaled 0.02. The culture was incubated at 37° C., 220 rpm for four hours to an $OD_{600}$=0.8. Induction of expression was compared at three different temperatures. Forty-five microliters of 100 mM IPTG was added to three 4.5 mL culture volumes (final IPTG concentration of 1 mM) and incubated at 37° C. for 3 hours, and 25° C. or 18° C. for 24 hours, all with shaking at 220 rpm. For lysate preparation, 1.5 mL and 1.0 mL culture volume from uninduced and induced cultures, respectively, were collected by centrifugation and resuspended in 300 µL of BUGBUSTER HT (EMD Sciences) and 3 µL Proteinase Inhibitor Cocktail (Sigma, St. Louis, Mo.). The mixtures were held on ice for 5 minutes and subsequently sonicated three times for ten seconds each with cooling in between. To obtain "soluble" and "insoluble" fractions the mixture was centrifuged at 14,000 rpm for five minutes at 4° C. The supernatant was designated "soluble" and the pellet was resuspended in 300 µL of BUGBUSTER HT and 3 µL Proteinase Inhibitor Cocktail and designated "insoluble". Protein concentration was determined by the BIO-RAD Protein Assay Dye Reagent system (BIO-RAD, Hercules, CA) according to the manufacturer's instructions.

For analysis of expression of ahpC (encoded by SEQ ID NO: 3) by COOMASSIE staining of SDS-PAGE gels, samples were subjected to electrophoresis on 4-15% gradient Tris-HCl Criterion gels (BIO-RAD) in 1×Tris glycine SDS buffer (BIO-RAD) under reducing and denaturing conditions. To estimate protein size, standards between 15 and 250 kDa (BIO-RAD) were run in parallel with the lysates. The gels were stained with BIO-SAFE COOMASSIE, a COOMASSIE G250 stain (BIO-RAD) according to the manufacturer's protocol.

A 24-kDa protein was specifically detected in lysates prepared from samples induced at all three temperature. Good expression was obtained at all three temperatures with ahpC localizing to both the soluble and insoluble fraction. Induction at 25° C. was the optimal temperature for producing soluble ahpC.

SEQ ID NO: 2 Purification

Direct scale-up of the above small scale procedure into stirred tank fermenters (30 liter scale) with a 20 liter working volume was achieved. Inoculum was cultivated in a 250 mL flask containing 50 mL of Luria-Bertani (LB) medium (plus ampicillin) and inoculated with 1 mL of frozen seed culture and cultivated for 6 hours. One mL of this seed was used to inoculate a 2 liter flask containing 500 mL of LB medium (plus ampicillin) and incubated for 16 hours. A large scale fermenter (30 liter scale) was cultivated with 20 liters of LB medium (plus ampicillin). The fermentation parameters of the fermenter were: pressure=5 psig, agitation speed=300 rpms, airflow=7.5 liters/minute and temperature=37° C. Cells were incubated to an optical density (OD) of 1.3 optical density snits, at a wavelength of 600 nm, and induced with Isopropyl-β-K-Thiogalactoside (IPTG) at a concentration of 1 mM. Induction time with IPTG was two hours. Cells were harvested by lowering the temperature to 15° C., concentrated by passage through a 500KMWCO hollow fiber cartridge, and centrifuged at 8,000 times gravity at 4° C. for 20 minutes. Supernatants were decanted and the recombinant E. coli wet cell pellets were frozen at −70° C.

Frozen recombinant E. coli cell paste (24 grams) was thawed and resuspended in two volumes of Lysis Buffer (50 mM sodium phosphate, pH 8.0, 0.15 M NaCl, 2 mM magnesium chloride, 10 mM imidazole, 20 mM 2-mercaptoethanol, 0.1% Tween-80, and protease inhibitor cocktail (COMPLETE™, EDTA-Free, Roche #1873580-one tablet per 50 mL Lysis Buffer). Benzonase (EM #1.01697.0002) was added to the cell suspension at 125 Units/mL). A lysate was prepared with a microfluidizer. The Lysate was stirred for three hours at 4° C., and was clarified by centrifugation at 10,000 ×g for 10 minutes at 4° C. The supernatant was filtered through a glass-fiber pre-filter Millipore and NaCl was added to a final concentration of 0.5 M from a 5 M stock solution. The Filtered Supernatant was added to Ni-NTA agarose chromatography resin (Qiagen #30250) and the slurry was mixed overnight at 4° C. The slurry of chromatography resin was poured into a chromatography column and the non-bound fraction was collected by gravity from the column outlet. The column was washed with ten column volumes of Wash Buffer (50 mM sodium phosphate, pH 8.0, 0.5 M NaCl, 2 mM magnesium chloride, 10 mM imidazole, 20 mM 2-mercaptoethanol, 0.1% Tween-80, and protease inhibitor cocktail (COMPLETE™, EDTA-Free, Roche #1873580-one tablet per 50 mL Wash Buffer). The column was eluted with Elution Buffer (50 mM sodium phosphate, pH 7.4, 0.3 M imidazole, 2 mM magnesium chloride, 0.1% Tween-80, and 20 mM 2-mercaptoethanol). Fractions containing protein were identified by dot blot on nitrocellulose membrane with Ponceau-S staining, and fractions containing the highest protein concentrations were pooled to make the Ni-IMAC Product. The Ni-IMAC Product was fractionated by SEC. SEC fractions containing the product protein were identified by SDS/PAGE with COOMASSIE staining. Product-containing SEC fractions were pooled to make the SEC Product. The SEC Product was sterile-filtered and adsorbed on aluminum hydroxyphosphate adjuvant at a final concentration of 0.2 mg/mL.

Preparation of S. aureus Challenge

S. aureus was grown on TSA plates at 37° C. overnight. The bacteria were washed from the TSA plates by adding 5 mL of PBS onto a plate and gently resuspending the bacteria with a sterile spreader. The bacterial suspension was spun at 6000 rpm for 20 minutes using a SORVALL RC-5B centrifuge (DuPont Instruments). The pellet was resuspended in 16% glycerol and aliquots were stored frozen at −70° C.

Prior to use, inocula were thawed, appropriately diluted and used for infection. Each stock was titrated at least 3 times to determine the appropriate dose inducing slow kinetics of death in naive mice. The potency of the bacterial inoculum (80 to 90% lethality) was constantly monitored to assure reproducibility of the model. Ten days before each challenge experiment, a group of 10 control animals (immunized with adjuvant alone) were challenged and monitored.

Protection Studies for a SEQ ID NO: 2 Polypeptide

In two independent experiments, twenty BALB/c mice each were immunized with three doses of SEQ ID NO: 2 polypeptide (20 μg per injection) on aluminum hydroxyphosphate adjuvant (450 μg per injection), and 20 mice each were injected with Aluminum hydroxyphosphate adjuvant (450 μg per injection). Aluminum hydroxyphosphate adjuvant (AHP) is described by Klein et al., *Journal of Pharmaceutical Sciences* 89: 311-321, 2000. The materials were administered as two 50 μL intramuscular injections on days 0, 7 and 21. The mice were bled on day 28, and their sera were screened by ELISA for reactivity to SEQ ID NO: 2.

Figure 6B:
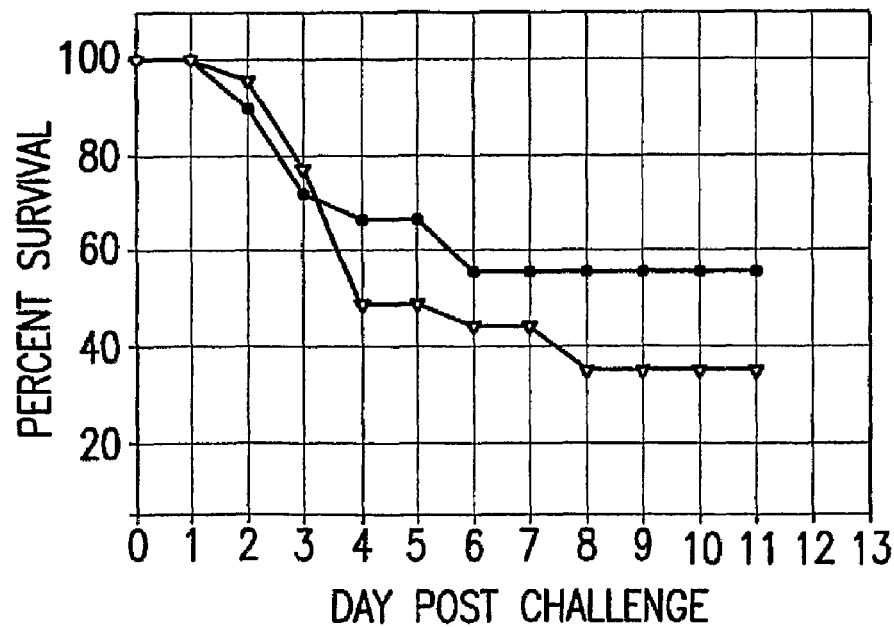

On day 35 of each experiment the mice were challenged by intravenous injection of *S. aureus* (dose $7 \times 10^8$ CFU/mL). The mice were monitored over a 11 day period for survival. At the end of the first experiment 12 mice survived in the SEQ ID NO: 2 polypeptide immunized group, compared to 5 surviving in the ASP control group. The results are illustrated in FIG. 6A. In the second experiment 11 mice survived in the SEQ ID NO: 2 polypeptide immunized group, compared to 7 surviving in the AHP control group. The results are illustrated in FIG. 6B.

Other embodiments are within the following claims. While several embodiments have been shown and described, various modifications may be made without departing from the spirit and scope of the present invention.

What is claimed is:

1. A purified polypeptide immunogen comprising an amino acid sequence with up to 9 amino acid alterations from SEQ ID NO: 1, wherein said polypeptide provides protective immunity against *S. aureus*, and wherein said polypeptide immunogen is not the polypeptide of SEQ ID NO: 1.

2. The polypeptide immunogen of claim 1, wherein said polypeptide is substantially purified.

3. The polypeptide immunogen of claim 1, wherein said amino acid sequence differs from SEQ ID NO: 1 by up to 5 amino acid alterations.

4. The polypeptide immunogen of claim 3, wherein said polypeptide is substantially purified.

5. The polypeptide immunogen of claim 3, wherein said amino acid sequence differs from SEQ ID NO: 1 by up to 3 amino acid alterations.

6. The polypeptide immunogen of claim 5, wherein said polypeptide is substantially purified.

7. The polypeptide immunogen of claim 1, wherein said polypeptide consists of amino acids 22-213 of SEQ ID NO: 2.

8. The polypeptide immunogen of claim 7, wherein said polypeptide is substantially purified.

9. A composition able to induce a protective immune response in a patient comprising an immunologically effective amount of the polypeptide immunogen of claim 1 and a pharmaceutically acceptable carrier.

10. A composition able to induce a protective immune response in a patient comprising an immunologically effective amount of the polypeptide immunogen of claim 3 and a pharmaceutically acceptable carrier.

11. A composition able to induce a protective immune response in a patient comprising an immunologically effective amount of the polypeptide immunogen of claim 5 and a pharmaceutically acceptable carrier.

12. An immunogen comprising a polypeptide consisting of an amino acid sequence with up to 9 amino acid alterations from SEQ ID NO: 1, wherein said polypeptide provides protective immunity against *S. aureus*, and one or more additional regions or moieties covalently joined to said amino acid sequence at the carboxyl terminus or amino terminus, wherein each region or moiety is independently selected from a region or moiety having at least one of the following properties: enhances the immune response, facilitates purification, or facilitates polypeptide stability.

13. The immunogen of claim 12, wherein said polypeptide differs from SEQ ID NO: 1 by up to 5 amino acid alterations.

* * * * *